United States Patent
Guy et al.

(10) Patent No.: US 11,701,330 B2
(45) Date of Patent: *Jul. 18, 2023

(54) USE OF CANNABINOIDS IN THE TREATMENT OF EPILEPSY

(71) Applicant: GW Research Limited, Cambridge (GB)

(72) Inventors: Geoffrey Guy, Cambridge (GB); Stephen Wright, Cambridge (GB); Orrin Devinsky, New York, NY (US)

(73) Assignee: GW Research Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/472,016

(22) Filed: Sep. 10, 2021

(65) Prior Publication Data

US 2021/0401771 A1 Dec. 30, 2021

Related U.S. Application Data

(63) Continuation of application No. 17/119,873, filed on Dec. 11, 2020, now Pat. No. 11,154,516, which is a (Continued)

(30) Foreign Application Priority Data

Jun. 17, 2014 (GB) .................................. 1410771
Apr. 17, 2015 (GB) .................................. 1506550

(51) Int. Cl.
| | | |
|---|---|---|
| A61K 31/05 | (2006.01) |
| A61K 31/195 | (2006.01) |
| A61K 31/20 | (2006.01) |
| A61K 31/27 | (2006.01) |
| A61K 31/352 | (2006.01) |
| A61K 31/4015 | (2006.01) |
| A61K 31/4166 | (2006.01) |
| A61K 31/423 | (2006.01) |
| A61K 31/496 | (2006.01) |
| A61K 31/53 | (2006.01) |
| A61K 31/551 | (2006.01) |
| A61K 31/5513 | (2006.01) |
| A61K 31/5517 | (2006.01) |
| A61K 31/7048 | (2006.01) |
| A61K 36/185 | (2006.01) |
| A61K 45/06 | (2006.01) |
| A61K 31/165 | (2006.01) |
| A61K 31/19 | (2006.01) |
| A61K 31/197 | (2006.01) |
| A61K 31/35 | (2006.01) |
| A61K 31/36 | (2006.01) |
| A61K 47/10 | (2017.01) |
| A61K 47/26 | (2006.01) |
| A61K 47/44 | (2017.01) |
| A61K 9/00 | (2006.01) |
| A61K 9/08 | (2006.01) |

(Continued)

(52) U.S. Cl.
CPC ............ *A61K 31/05* (2013.01); *A61K 9/0053* (2013.01); *A61K 9/08* (2013.01); *A61K 31/165* (2013.01); *A61K 31/19* (2013.01); *A61K 31/195* (2013.01); *A61K 31/197* (2013.01); *A61K 31/20* (2013.01); *A61K 31/27* (2013.01); *A61K 31/35* (2013.01); *A61K 31/352* (2013.01); *A61K 31/36* (2013.01); *A61K 31/4015* (2013.01); *A61K 31/4166* (2013.01); *A61K 31/423* (2013.01); *A61K 31/444* (2013.01); *A61K 31/496* (2013.01); *A61K 31/515* (2013.01); *A61K 31/53* (2013.01); *A61K 31/55* (2013.01); *A61K 31/551* (2013.01); *A61K 31/5513* (2013.01); *A61K 31/5517* (2013.01); *A61K 31/7048* (2013.01); *A61K 36/185* (2013.01); *A61K 45/06* (2013.01); *A61K 47/10* (2013.01); *A61K 47/26* (2013.01); *A61K 47/44* (2013.01)

(58) Field of Classification Search
CPC ..................................................... A61K 31/05
See application file for complete search history.

(56) References Cited

U.S. PATENT DOCUMENTS 2,304,669 A 12/1942 Adams
6,383,513 B1 5/2002 Watts et al.
(Continued)

FOREIGN PATENT DOCUMENTS

CA 2737447 A1 10/2012
CA 2859934 A1 3/2016
(Continued)

OTHER PUBLICATIONS

Field et al. The Ethical Conductor Clinical Research Involving Children, The National Academies Press, 2004, pp. 1-446 (Year: 2004).*

(Continued)

*Primary Examiner* — Matthew P Coughlin
(74) *Attorney, Agent, or Firm* — Cooley LLP

(57) ABSTRACT

The present disclosure relates to the use of cannabidiol (CBD) for the reduction of total convulsive seizure frequency in the treatment of "treatment-resistant epilepsy" (TRE). In particular, the disclosure relates to the use of CBD of treating TRE when the TRE is Dravet syndrome; myoclonic absence seizures or febrile infection related epilepsy syndrome (FIRES). The disclosure further relates to the use of CBD in combination with one or more anti-epileptic drugs (AEDs).

30 Claims, No Drawings

Related U.S. Application Data continuation of application No. 16/791,940, filed on Feb. 14, 2020, now abandoned, which is a continuation of application No. 15/948,412, filed on Apr. 9, 2018, now Pat. No. 10,603,288, which is a continuation of application No. 15/449,084, filed on Mar. 3, 2017, now Pat. No. 9,956,183, which is a continuation of application No. 15/284,766, filed on Oct. 4, 2016, now Pat. No. 9,949,936, which is a continuation of application No. 14/741,783, filed on Jun. 17, 2015, now Pat. No. 9,474,726.

(51) Int. Cl.
*A61K 31/444* (2006.01)
*A61K 31/515* (2006.01)
*A61K 31/55* (2006.01)

(56) References Cited

U.S. PATENT DOCUMENTS

| | | |
|---|---|---|
| 6,949,582 B1 | 9/2005 | Wallace |
| 7,025,992 B2 | 4/2006 | Whittle et al. |
| 8,293,786 B2 | 10/2012 | Stinchcomb |
| 8,673,368 B2 | 3/2014 | Guy et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,522,123 B2 | 12/2016 | Whalley et al. |
| 9,949,936 B2 | 4/2018 | Guy et al. |
| 9,949,937 B2 * | 4/2018 | Guy ............... A61P 25/00 |
| 9,956,183 B2 * | 5/2018 | Guy ............... A61K 31/19 |
| 9,956,184 B2 * | 5/2018 | Guy ............... A61K 31/5513 |
| 9,956,185 B2 | 5/2018 | Guy et al. |
| 9,956,186 B2 * | 5/2018 | Guy ............... A61P 43/00 |
| 10,092,525 B2 | 10/2018 | Guy et al. |
| 10,111,840 B2 | 10/2018 | Guy et al. |
| 10,137,095 B2 | 11/2018 | Guy et al. |
| 10,583,096 B2 | 3/2020 | Guy et al. |
| 10,603,288 B2 * | 3/2020 | Guy ............... A61K 47/10 |
| 10,709,671 B2 | 7/2020 | Guy et al. |
| 10,709,673 B2 | 7/2020 | Guy et al. |
| 10,709,674 B2 * | 7/2020 | Guy ............... A61P 25/08 |
| 10,765,643 B2 | 9/2020 | Guy et al. |
| 10,807,777 B2 | 10/2020 | Whittle |
| 10,849,860 B2 * | 12/2020 | Guy ............... A61P 25/08 |
| 10,918,608 B2 | 2/2021 | Guy et al. |
| 10,925,525 B2 | 2/2021 | Nakaji |
| 10,966,939 B2 | 4/2021 | Guy et al. |
| 11,065,209 B2 | 7/2021 | Guy et al. |
| 11,065,227 B2 | 7/2021 | Stott et al. |
| 11,096,905 B2 * | 8/2021 | Guy ............... A61P 43/00 |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Guy et al. |
| 11,160,757 B1 | 11/2021 | Wilkhu et al. |
| 11,160,795 B2 | 11/2021 | Guy et al. |
| 11,207,292 B2 * | 12/2021 | Guy ............... A61K 31/05 |
| 11,311,498 B2 | 4/2022 | Guy et al. |
| 11,357,741 B2 * | 6/2022 | Guy ............... A61K 47/10 |
| 11,400,055 B2 | 8/2022 | Guy et al. |
| 11,406,623 B2 | 8/2022 | Guy et al. |
| 11,426,362 B2 | 8/2022 | Wright et al. |
| 11,446,258 B2 | 9/2022 | Guy et al. |
| 2004/0034108 A1 | 2/2004 | Whittle |
| 2004/0110828 A1 | 6/2004 | Chowdhury et al. |
| 2004/0147767 A1 | 7/2004 | Whittle et al. |
| 2005/0266108 A1 | 12/2005 | Flockhart et al. |
| 2006/0039959 A1 | 2/2006 | Wessling |
| 2006/0167283 A1 | 7/2006 | Flockhart et al. |
| 2008/0112895 A1 | 5/2008 | Kottayil et al. |
| 2008/0119544 A1 | 5/2008 | Guy et al. |
| 2008/0188461 A1 | 8/2008 | Guan |
| 2009/0036523 A1 | 2/2009 | Stinchcomb et al. |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 2/2011 | Guy et al. |
| 2011/0150825 A1 | 6/2011 | Buggy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0270845 A1 | 10/2012 | Bannister |
| 2013/0143894 A1 | 6/2013 | Bergstrom et al. |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0342902 A1 | 12/2015 | Vangara et al. |
| 2015/0343071 A1 | 12/2015 | Vangara et al. |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0224634 A1 | 8/2017 | Vangara et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Wilkhu et al. |
| 2018/0071210 A1 | 3/2018 | Wilkhu et al. |
| 2018/0228751 A1 | 8/2018 | Stott et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206152 A1 | 7/2020 | Stott et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2020/0368179 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0093581 A1 | 4/2021 | Guy et al. |
| 2021/0145765 A1 | 5/2021 | Guy et al. |
| 2021/0169824 A1 | 6/2021 | Guy et al. |
| 2021/0177773 A1 | 6/2021 | Guy et al. |
| 2021/0196651 A1 | 7/2021 | Guy et al. |
| 2021/0290565 A1 | 9/2021 | Guy et al. |
| 2021/0330636 A1 | 10/2021 | Guy et al. |

(56) References Cited

U.S. PATENT DOCUMENTS

| | | | |
|---|---|---|---|
| 2022/0000800 A1 | 1/2022 | Guy et al. | |
| 2022/0395471 A1 | 12/2022 | Guy et al. | |

FOREIGN PATENT DOCUMENTS

| | | | |
|---|---|---|---|
| CN | 101040855 A | 9/2007 | |
| CN | 103110582 A | 5/2013 | |
| EP | 2 448 637 B1 | 5/2012 | |
| EP | 3 157 512 B1 | 5/2018 | |
| GB | 2 377 633 A | 1/2003 | |
| GB | 2 380 129 A | 4/2003 | |
| GB | 2 381 194 A | 4/2003 | |
| GB | 2384707 A | 8/2003 | |
| GB | 2434097 A | 7/2007 | |
| GB | 2434312 A | 7/2007 | |
| GB | 2450753 A | 1/2009 | |
| GB | 2456183 A | 7/2009 | |
| GB | 2471523 A | 1/2011 | |
| GB | 2478595 A | 9/2011 | |
| GB | 2479153 A | 10/2011 | |
| GB | 2 485 291 A | 5/2012 | |
| GB | 2 487 183 A | 7/2012 | |
| GB | 2471565 B | 7/2012 | |
| GB | 2478072 B | 12/2012 | |
| GB | 2478074 B | 12/2012 | |
| GB | 2492487 A | 1/2013 | |
| GB | 2487712 A | 10/2015 | |
| GB | 2 530 001 A | 3/2016 | |
| GB | 2531282 A | 4/2016 | |
| GB | 2539472 A | 12/2016 | |
| WO | WO 01/95899 A2 | 12/2001 | |
| WO | WO 2002/064109 A2 | 8/2002 | |
| WO | WO 02/089945 A2 | 11/2002 | |
| WO | WO 2003/099302 A1 | 12/2003 | |
| WO | WO 2004/016246 A1 | 2/2004 | |
| WO | WO 2004/016277 A2 | 2/2004 | |
| WO | WO 2004/026802 A1 | 4/2004 | |
| WO | WO 2006/054057 A2 | 5/2006 | |
| WO | WO 2006/017892 A1 | 12/2006 | |
| WO | WO 2006/133941 A2 | 12/2006 | |
| WO | WO 2007/052013 A1 | 5/2007 | |
| WO | WO 2007/083098 A1 | 7/2007 | |
| WO | WO 2007/138322 A1 | 12/2007 | |
| WO | WO 2008/094181 A3 | 8/2008 | |
| WO | WO 2008/129258 A1 | 10/2008 | |
| WO | WO 2008/021394 A2 | 12/2008 | |
| WO | WO 2008/146006 A1 | 12/2008 | |
| WO | WO 2009/007697 A1 | 1/2009 | |
| WO | WO 2009/093018 A1 | 7/2009 | |
| WO | WO 2011/001169 A1 | 1/2011 | |
| WO | WO 2011/121351 A1 | 10/2011 | |
| WO | WO 2012/093255 A1 | 7/2012 | |
| WO | WO 2012/160358 A1 | 11/2012 | |
| WO | WO 2013/032351 A1 | 3/2013 | |
| WO | WO 2013/045891 A1 | 4/2013 | |
| WO | WO 2015/142501 A1 | 9/2015 | |
| WO | WO 2015/184127 A2 | 12/2015 | |
| WO | WO 2015/193667 A1 | 12/2015 | |
| WO | WO 2015/193668 A1 | 12/2015 | |
| WO | WO 2016/059403 A1 | 4/2016 | |
| WO | WO 2016/059405 A1 | 4/2016 | |
| WO | WO 2015/187988 A1 | 7/2016 | |
| WO | WO 2016/118391 A1 | 7/2016 | |
| WO | WO 2016/022936 A1 | 11/2016 | |
| WO | WO 2016/203239 A1 | 12/2016 | |
| WO | WO 2018/234811 A1 | 12/2018 | |

OTHER PUBLICATIONS

FDA, Guidance for Industry Drug-Induced Liver Injury: Premarketing Clinical Evaluation, Jul. 2009, pp. 1-25 (Year: 2009).*
U.S. Appl. No. 14/741,829, filed Jun. 17, 2015.
U.S. Appl. No. 15/519,244, filed Apr. 14, 2017.
U.S. Appl. No. 15/640,033, filed Jun. 30, 2017.
U.S. Appl. No. 16/314,569, filed Dec. 31, 2018.
U.S. Appl. No. 16/314,583, filed Dec. 31, 2018.
U.S. Appl. No. 16/467,639, filed Jun. 7, 2019.
U.S. Appl. No. 16/486,750, filed Aug. 16, 2019.
U.S. Appl. No. 16/624,106, filed Dec. 18, 2019.
U.S. Appl. No. 16/651,751, filed Mar. 27, 2020.
U.S. Appl. No. 16/737,707, filed Jan. 8, 2020.
U.S. Appl. No. 16/764,701, filed May 15, 2020.
U.S. Appl. No. 16/768,241, filed May 29, 2020.
U.S. Appl. No. 16/893,018, filed Jun. 4, 2020.
U.S. Appl. No. 16/935,005, filed Jul. 21, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/960,665, filed Jul. 8, 2020.
U.S. Appl. No. 17/011,715, filed Sep. 3, 2020.
U.S. Appl. No. 17/025,130, filed Sep. 18, 2020.
U.S. Appl. No. 17/050,956, filed Oct. 27, 2020.
U.S. Appl. No. 17/296,066, filed May 21, 2021.
U.S. Appl. No. 17/296,076, filed May 21, 2021.
U.S. Appl. No. 14/340,885, filed Jun. 7, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/470,382, filed Sep. 9, 2021.
U.S. Appl. No. 17/472,000, filed Sep. 10, 2021.
U.S. Appl. No. 17/477,172, filed Sep. 16, 2021.
U.S. Appl. No. 17/606,370, filed Oct. 25, 2021.
Notice of Opposition to European Patent Application No. EP15784111.5, Patent No. EP3206716, dated May 10, 2021.
[Anonymous], "GW Pharma—GW Pharmaceuticals Announces New Physician Reports of Epidiolex® Treatment Effect in Children and Young Adults With Treatment-Resistant Epilepsy," Oct. 14, 2014; https://ir.gwpharm.com/news-releases/news-release-details/gw-pharmaceuticals-announces-new-physician-reports-epidiolexr-0, 4 pages.
[Anonymous], "GW Pharmaceuticals Announces Epidiolex Receives Fast Track Designation from FDA for the Treatment of Dravet Syndrome," GW Pharmaceuticals Press Release dated Jun. 6, 2014; http://www.gwpharm.com/GW%20Pharmaceuticals%20Announces%20Epidiolex%20Receives%20Fast%20Track%20Designation%20from%20FDA%20for%20the%20Treatment%20of%20Dravet%20Syndrome.aspx, 5 pages.
[Anonymous], "Salutaris Drops Buy Salutaris Drops—Salutaris Drops," Oct. 12, 2014; http://web.archive.org/web/20141012130255/http://salutarisdrops.com/buy-salutaris-drops/, 2 pages.
[Anonymous], "GW Pharmaceuticals Receives Orphan Drug Designation by FDA for Epidiolex® in the Treatment of Lennox-Gastaut Syndrome," GW Pharmaceuticals Press Release, Feb. 28, 2014; https://www.gwpharm.com/ir/press-releases/gw-pharmaceuticals-receives-orphan-drug-designation-fda-epidiolexr-treatment, 4 pages.
[Anonymous], "Salutaris Drops Cannabidiol for Aicardi Syndrome—Salutaris Drops," Oct. 12, 2014; http://web.archive.org/web/20141012220050/http://salutarisdrops.com/cannabidiol-aicardi-syndrome/, 3 pages.
[Anonymous], "GW Pharma Initiates Second Phase 3 Pivotal Study of Epidiolex® (CBD) in Lennox-Gastaut Syndrome," Jun. 11, 2015; https://www.benzinga.com/pressreleases/18/11/g12748407/gw-pharmaceuticals-announces-second-positive-phase-3-pivotal-trial-for, 5 pages.
Booth, "Legalization's opening of medical pot research is dream and nightmare," Denver Post, Dec. 14, 2013, http://www.denverpost.com/ci_24726291/legalizations-opening-medical-pot-research-is-dream-and, 6 pages.
[No Author Listed], "ILAE Proposal for Revised Terminology for Organization of Seizures and Epilepsies," 2010, 2 pages.
[No Author Listed] "Orphan Drug Designation Granted for Epidiolex in Dravet syndrome by the FDA-Seven Expanded Access INDs granted by FDA to US physicians to treat with Epidiolex 125 children suffering from intractable epilepsy syndromes," GW Pharmaceuticals Press Release dated Nov. 14, 2013.

(56) References Cited

OTHER PUBLICATIONS

[No Author Listed] GW Pharmaceuticals Provides Update on Orphan Program in Childhood Epilepsy for Epidiolex, GW. Pharm. Available online Nov. 14, 2013, Retrieved Feb. 10, 2017.
[No Author Listed] "What are the Highest CBD Strains?" accessed Feb. 16, 2017, published Oct. 15, 2014.
[No Author Listed] "Cannabidiol Therapy for Aicardi Syndrome" Aug. 2014, 4 pages.
[No Author Listed] "Convulsive Disorders and Their Interference with Driving," Medicos., Retrieved Feb. 10, 2017, Retrieved from internet: URL https://www.medicosporlaseguridadvial.com/en/clinical-subjects/neurologic-diseases/convulsive- disorders-and-their-interference-with-driving/, 2014.
[No Author Listed] "Estimating the Maximum Safe Starting Dose in Initial Clinical Trials for Therapeutics in Adult Healthy Volunteers," FDA Guidance for Industry, Jul. 2005.
[No Author Listed] "GW Pharmaceuticals Announces Physician Reports of Epidiolex Treatment Effect in Children and Young Adults with Treatment-resistant epilepsy from Physician-Led Expanded Access Treatment Program," GW Pharmaceuticals Press Release dated Jun. 17, 2014.
[No Author Listed], "Missouri House passes cannabis extract legislation," Kansas City Star, 2014, https://kansascity.com/news/politics-government/article346747.html, 2 pages.
Alger, B. E., "Not too excited? Thank your endocannabinoids," Neuron, 51(4):393-595 (2006).
American Epilepsy Society, Three Studies Shed New Light on the Effectiveness of Cannabis in Epilepsy, Oct. 14, 2014, 2 pages.
Ames, F. R. et al., "Anticonvulsant effect of cannabidiol," S Afr Med J. Jan. 4, 1986; 69(1):14, 1 page.
AAN 67th Annual Meeting Abstract, Apr. 2015; https://www.aan.com/PressRoom/Home/GetDigitalAsset/11570, 1 page.
Annex to the Communication-Opposition for Application No. 10734541.5, dated Jan. 28, 2016.
Arain, A. M., "Pregabalin in the management of partial epilepsy," Neuropsychiatr Dis Treat., 407-13 (2009); Epub Aug. 20, 2009.
Arslan, A. & Tirnaksiz, F., "Self-emulsifying Drug Delivery Systems," F ABAD J Pharm Sci, 38(1):55-64 (2013).
Avoli, M. et al., "Cellular and molecular mechanisms of epilepsy in the human brain," Prog Neurobiol., 77(3):166-200 (2005).
Babayeva et al., "Marijuana Compounds: A Non-Conventional Therapeutic Approach to Epilepsy in Children," J. Addict. Neuropharmacol, 1:1 (2014); doi: 10.24966/AAD-7276/100002, 9 pages.
Bakhsh, K., "Pregabalin in the management of partial epilepsy," Miftaah-al-Khazaain, 1930:607-608, with English translation, 4 pages.
Bancaud, et al., "Proposal for Revised Clinical and Electroencephalographic Classification of Epileptic Seizures," Epilepsia, 22(4):489-501 (1981).
Barker-Haliski, M. et al., "How Clinical Development Can, and Should Inform Translational Science," Neuron, 84:582-593 (2014).
Benowitz, N. L. et al., "Metabolic and Psychophysiologic studies of cannabidiol hexobarbital interaction," Clin Pharmacol Ther., 28(1):115-120 (1980).
Bertram, E., "The Relevance of Kindling for Human Epilepsy," Epilepsia, 48(Suppl. 2):65-74 (2007).
Bipolar Health Group (Charlotte's Web Hemp Remedy, available online at http:/bipolarhealthgroup.org/index.php/charlottes-web-hemp-remedy/, accessed Sep. 6, 2017.
Bhatt, V. P. & Vashishtha, D. P., "Indigenous plants in traditional healthcare system in Kedarnath valley of western Himalaya," Indian J Tradit Knowl., 7(2):300-310 (2000).
Bhattacharyya, S. et al., "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi: 10.1001/archgenpsychiatry. 2009 .17.

Bostanci, M. O. & Bagirici, F., "The effects of octanol on penicillin induced epileptiform activity in rats: an in vivo study," Epilepsy Research, 71:188-194 (2006).
Braida, D. et al., "Post-ischemic treatment with cannabidiol prevents electroencephalographic flattening, hyperlocomotion and neuronal injury in gerbils," Neuroscience Letters., 346:61-64 (2003).
Brown et al., Child Neurology Foundation, "LGS" (Lennox-Gastaut Syndrome), available at http://www.childneurologyfoundation.org/disorders/lgs-lennox-gastaut-syndrome.
Brust, J. C. M. et al., "Marijuana use and the risk of new onset seizures," Trans Am Clin Climatol Assoc., 103:176-181 (1992).
"Cannabidiols: Potential Use in Epilepsy & Other Neurological Disorders." Cannabidiol Conference at NYU School of Medicine, Oct. 2013. NYU Langone Health. Retrieved from the Internet Nov. 2019. <URL: http://faces.med.nyu.edu/research-education/cannabidiol-conference>, 4 pages.
Camfield, "Definition and natural history of Lennox-Gastaut Syndrome," Epilepsia, 52:3-9 (2011).
Campos-Castello, "Rational approach to treatment options for Lennox-Gastaut syndrome," Orphanet, Mar. 2003; https://www.orpha.net/data/patho/GB/uk-Lennox.pdf, 5 pages.
Carlini, et al., "Hypnotic and antiepileptic effects of cannabidiol," J Clin Pharmacol. Aug.-Sep. 1981;21(8-9 Suppl):417S-427S. Medline abstract only.
Castel-Branco, et al., "The Maximal Electroshock Seizure (MES) Model in the Preclinical 98. Assessment of Potential New Anti epileptic Drugs," Methods Find Exp Clin Pharmacol., 31(2): 101-106 (2009).
Charlotte's [ Web online], "Whole-Plant Cannabinoids Outperform Single Molecule Compounds," CWHemp.com, Jan. 11, 2017, retrieved on Jun. 16, 2017, URL https://www.cwhemp.com/blog/whole-plant-cw-hemp-cannabinoids, 6 pages.
Chiron, C. & DULAC, O., "The Pharmacologic Treatment of Dravet Syndrome," Epilepsia, 52 (Suppl. 2):72-75 (2011).
Chiu, P. et al., "The Influence of Cannabidiol and Δ-Tetrahydrocannabinol on Cobalt Epilepsy in Rats," Epilepsia, 20:365-375 (1979).
Ciccone, "Drop Seizure Frequency in Lennox-Gastaut Decrease With Cannabidiol," Neurology Advisor, Apr. 26, 2017; retrieved from the Internet: URL:https://neurologyadvisor.com/aan-2017-coverage/aan-2017-cannabidiol-reduces-drop-seizures-in-lennox-gasaut-syndrome/article/652931.
Cilio, Maria Roberta, M.D., Ph.D. of the Pediatric Epilepsy and Clinical Neurophysiology for the University of California, San Francisco presents her talk on "CBD in Children with Treatment-Resistant Epilepsies: Planned Trials in Dravet and Lennox-Gastaut Syndromes," at NYU School of Medicine's Cannabidiol Conference (Oct. 4, 2013). Video published online, <http://faces.med.nyu.edu/research-education/cannabidiol-conference>.
Citti et al., "Pharmaceutical and biomedical analysis of cannabinoids: A critical review," Journal of Biopharmaceutical and Biomedical Analysis, 147:565-579 (2018).
Combined Search and Examination Report dated Jan. 4, 2012 for Application No. GB 1116789.7.
Combined Search and Examination Report dated Mar. 25, 2011 for Application No. GB 1100043.7.
Combined Search and Examination Report dated Sep. 5, 2014 for Application No. GB 1414813 .4 .
Combined Search and Examination Report Under Sections 17 and 18 (3) for International Application No. GB1121919.3, dated Feb. 29, 2012.
Combined Search and Examination Report Under Sections 17 and 18 (3) for International Application No. GB 1410771.8, dated Feb. 27, 2018.
Combined Search and Examination Report Under Sections 17 and 18 (3) for International Application No. GB 1418166.3, dated Jul. 2, 2015.
Combined Search and Examination Report Under Sections 17 and 18 (3) for International Application No. GB 1418170.5, dated Jul. 2, 2015.
Combined Search and Examination Report Under Sections 17 and 18 (3) for International Application No. GB 1418171.3, dated Jun. 29, 2015.

(56) References Cited

OTHER PUBLICATIONS

Combined Search and Examination Report Under Sections 17 and 18 (3) for International Application No. GB 1506550.1, dated Feb. 5, 2016.
Combined Search and Examination Report for GB Application No. GB1611544.6, dated Mar. 29, 2017, 8 pages.
Combined Search and Examination Report for GB Application No. GB1514079.1, dated May 4, 2016, 9 pages.
Combined Search and Examination Report for GB Application No. GB160544.8, dated Jan. 12, 2017, 6 pages.
Combined Search and Examination Report for GB Application No. GB1621480.1, dated Sep. 22, 2017.
Communication of a Notice of Opposition for Application No. 107342541.5 dated Dec. 17, 2014.
Communication Pursuant to Article 94(3) EPC in European Patent Application No. 10734541.5, dated Oct. 23, 2012.
Conry, J. A. et al., "Clobazam in the treatment of Lennox-Gastaut syndrome," Epilepsia, 50:1158-1166 (2009).
Consroe, et al., "Anticonvulsant drug antagonism of delta9tetrahydrocannabinol-induced seizures in rabbits," Res Commun Chem Pathol Pharmacol., 16(1):1-13 (1977).
Consroe, et al., "Anticonvulsant interaction of cannabidiol and ethosuximide in rats," J Pharm Pharmacol., 29(8):500-501 (1977); doi: 10.1111/j.2042-7158.1977.tb11378.x.
Consroe, et al., "Anticonvulsant nature of marihuana smoking," JAMA, 234(3):306-307 (1975).
Consroe, et al., "Cannabidiol—antiepileptic drug comparisons and interactions in experimentally induced seizures in rats," J Pharmacol Exp Ther., 201(1):26-32 (1977).
Consroe, et al., "Controlled clinical trial of cannabidiol in Huntington's Disease," Pharmacology Biochemistry & Behavior, 40:701-708 (1991).
Consroe, et al., "Effects of cannabidiol on behavioral seizures caused by convulsant drugs or current in mice," Eur J Pharmacol., 83(3-4):293-298 (1982).
Consroe, et al. Chapter 12, "Potential Role of Cannabinoids for Therapy of Neurological Disorders." p. 459 in Marijuana Cannabinoids: Neurobiology and Neurophysiology, ed. L. Murphy (1992).
Cortesi, et al., "Potential therapeutical effects of cannabidiol in children with pharmacoresistant epilepsy," Med Hypotheses, 68(4):920-921 2007). Epub Nov. 16, 2006.
Cortez, et al. Chapter 10, "Pharmacologic Models of Generalized Absence Seizures in Rodents," Models of Seizures and Epilepsy, 111-126 (2006).
Crespel, A. et al., "Lennox-Gastaut Syndrome," Chapter 14, in Epileptic Syndromes in Infancy, Childhood, and Adolescence, 5th Edition, ed. M. Bureau, et al., pp. 189-216.
Cunha, et al., "Chronic administration of cannabidiol to healthy volunteers and epileptic patients," Pharmacology, 21 (3):175-85 (1980).
Czapinski, et al., "Randomized 36-month comparative study of valproic acid (VPA), phenytoin (PHT), phenobarbital (PB) and carbamazepine (CBZ) efficacy in patients with newly diagnosed epilepsy with partial complex seizures," J Neurolog Sci., 150:S162 (1997).
Dasa, et al. "Brhat Nighantu Ratnakara (Saligramanighantubhusanam)." vol. IV. 1997:170. Sanskrit. Exhibit 5.
Davis, et al., "A predominant role for inhibition of the adenylate cyclase/protein kinase. A pathway in ERK activation by cannabinoid receptor 1 in NIE-115 neuroblastoma cells," J Biol Chem., 278(49):48973-80 (2003). Epub Sep. 29, 2003.
Davis, et al., "Antiepileptic action of marijuana-active substances," Federation Proceedings, 8:284-5 (1949).
Decision in IPR2017-00503 dated Jul. 7, 2017.
Decision in Opposition proceedings (Art. 101(3)(a) and 106(2) EPC in European Patent Application No. EP2448637, dated Dec. 15, 2016.

Deshpande, et al., "Cannabinoid CB 1 receptor antagonists cause status epilepticus-like activity in the hippocampal neuronal culture model of acquired epilepsy," Neurosci Lett., 41 I(I):1-6 (2007). Epub Nov. 15, 2006.
De Oliveira, et al., "Anticonvulsant activity of β-caryophyllene against pentylenetetrazol-induced seizures," Epilepsy Behav., 56:26-31 (2016); doi: 10.1016/j.yebeh.2015.12.040.
De Meijer, "The Chemical Phenotypes (Chemotypes) of Cannabis," Chapter 5, Handbook of Cannabis, ed. Roger G. Pertwee, pp. 89-110 (2014).
Devinsky, Orrin, M.D. of the Department of Neurology for NYU Langone School of Medicine presents his talk on "Cannabidiols: A Brief History," at NYU School of Medicine's Cannabidiol Conference (Oct. 4, 2013). Video published online, <http://faces.med.nyu.edu/research-education/cannabidiol-conference>.
Devinsky et al., "Epidiolex (Cannabidiol) in Treatment Resistant Epilepsy," Apr. 2015; https://epilepsyontario.org/wp-content/uploads/2015/Epidiolex-Cannabidiol-in-Treatment-Resistant-EpilepsyAAN-POSTER08Apr2015.pdf, 1 page.
Devinsky, et al., "Cannabidiol: Pharmacology and potential therapeutic role in epilepsy and other neuropsychiatric disorders," Epilepsia, 55(6):791-802 (2014).
Devinsky et al., "Efficacy and safety of Epidiolex (cannabidiol) in children and young adults with treatment-resistant epilepsy: Initial data from expanded access program," Jan. 2015.
Devinsky et al., "Cannabidiol in patients with treatment-resistant epilepsy: an open-label interventional trial," Lancet Neurology, 15(3):270-278 (2015).
Devinsky et al., "Cannabidiol (CBD) significantly reduces drop seizure frequency in Lennox-Gastaut syndrome (LGS): results of a dose-ranging, multi-center, randomized, double-blind, placebo-controlled trial (GWPCARE3)," Epilepsia, 58:S13-S14 (2017).
Devinsky et al., "Trial of Cannabidiol for Drug-Resistant Seizures in the Dravet Syndrome," N Engl J Med, 376(21):2011-2020 (2017).
Di Marzo, Vincenzo, Ph.D. of the Endocannabinoid Research Group Istituto di Chimica Biomolecolare, Consiglio Nazionale delle Ricerche, Pozzuoli, Napoli, Italy presents his talk on "Cannabinoid Pharmacology & Mechanism of Action," at NYU School of Medicine's Cannabidiol Conference (Oct. 4, 2013). Video published online, <http://faces.med.nyu.edu/research-education/cannabidiol-conference>.
Dravet, "The core Dravet syndrome phenotype," Epilepsia, 52 Suppl 2:3-9 (2011); doi: 10.1111/j.1528-1167.2011.02994.x.
Dreifus, et al., "Proposal for Revised Clinical and Electroencephalographic Classification of Epileptic Seizures," Epilepsie., 22:489-501 (1981).
Drugs of the Future, 39(1): 49-56, Jan. 2014 notes Orphan Drug designation for CBD for Lennox-Gastaut Syndrome.
Dulac, "Use of Lamotrigine in Lennox-Gastaut and Related Epilepsy Syndromes," J. Child Neurolog., 12(Supplement1):S23-S29(1997).
Dulac, "Vigabatrin in Childhood Epilepsy," J. Child Neurolog., 6(Supplement2): S30-S37 (1991).
Eadie, "Shortcomings in the current treatment of epilepsy," Expert Rev Neurother., 12(12): 1419-27 (2012).
Engel, "Report of the ILAE classification core group," Epilepsia, 47(9):1558-68 (2006).
Engel, "What should be modeled," in Models Seizure Epilepsy, 2006, 14 pages.
Eggers, "Temporal lobe epilepsy is a disease of faulty neuronal resonators rather than oscillators, and all seizures are provoked, usually by stress," Med Hypotheses.,69(6):1284-9 (2007).
Elsohly and Gul, "Constituents of Cannabis Sariva," Chapter 1, Handbook of Cannabis, Roger G. Pertwee, Ed., pp. 3-22 (2014).
EPO Reply to Proprietor's Statement of Grounds of Appeal for European Patent No. EP2448637, dated Sep. 8, 2017, 5 pages.
EPO Response to the Statement of Grounds of Appeal for European Patent No. EP2448637, dated Sep. 5, 2017, 17 pages.
EPO Auxiliary Requests to the File in European Patent No. EP2448637, dated Nov. 2, 2016.
EPO Interlocutory Decision in Opposition in European Application No. EP2448637, Dec. 15, 2016.

(56) References Cited

OTHER PUBLICATIONS

EPO Letter from Opponent Regarding Oral Proceedings in European Patent No. EP2448637, dated Oct. 20, 2016.
Ex parte Edelstam, Appeal No. 2016/006358, mail date Jun. 21, 2017 (Year: 2017).
Ex parte Miller, Appeal 2009-011751, mail date Jul. 8, 2010 (Year: 2010).
Examination Report dated Mar. 18, 2014 for Application No. GB1100043.7.
Expert Statement of Vincenzo Di Marzo for Application No. EP10734541.5 dated Sep. 9, 2016.
Expert Statement of Professor Benjamin J. Whalley for Application No. EP10734541.5 dated Sep. 9, 2016.
Expert Statement of Professor Anthony G. Marson for Application No. EP10734541.5.
Expert Statement of Dr. Emma Louise Cheetham in European Application No. EP10743541.5, dated Nov. 4, 2016.
FDA, "Warning Letters and Test Results for Cannabidiol-Related Products," 2016 Warning Letters.
FDA, "Warning Letters and Test Results for Cannabidiol-Related Products," 2015 Warning Letters.
Fariello, "Parenteral Penicillin in Rats: An Experimental Model of Multifocal Epilepsy," Epilepsia, 17:217-222 (1976).
Ferdinand, et al., "Cannabis—psychosis pathway independent of other types of psychopathology," Schizophr Res., 79(2-3):289-295 (2005).
Fisher, et al., "The impact of epilepsy from the patient's perspective I. Descriptions and subjective perceptions," Epilepsy Res.,41(1):39-51 (2000).
French, Jacqueline A., M.D. Professor of Neurology at the NYU Epilepsy Center presents her talk on "Trials for Disease Modifying Therapies in Epilepsy," at NYU School of Medicine's Cannabidiol Conference (Oct. 4, 2013). Video published online, <http://faces.med.nyu.edu/research-education/cannabidiol-conference>.
Friedman, Daniel, M.D. Assistant Professor of Neurology at the NYU Comprehensive Epilepsy Center presents his talk on "Pharmacology of CBD in Humans," at NYU School of Medicine's Cannabidiol Conference (Oct. 4, 2013). Video published online, <http://faces.med.nyu.edu/research-education/cannabidiol-conference>.
Gabor, et al., "Lorazepam versus phenobarbital: Candidates for drug of choice for treatment of status epilepticus," J Epilepsy, 3(1):3-6 (1990).
Galliy, et al., "Overcoming the Bell-Shaped Dose-Response of Cannabidiol by Using Cannabis Extract Enriched in Cannabidiol," Pharmacology & Pharmacy, 6:75-85 (2015).
Gastaut, "Clinical and electroencephalographical classification of epileptic seizures," Epilepsia, 10:Suppl:2-13 (1969).
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda-approves-ind-studies-of-cbd, 4 pages.
Gedde, Retrospective Case Review of High CBD, Low THC Cannabis Extract (Realm Oil) for Intractable Seizure Disorders, 2013 Realm of Caring Foundation, 4 pages.
Gedde, "Clinical Experience with Cannabis in Treatment-Resistant Pediatric Epilepsy," http://www.theroc.us/images/gedde presentation.pdf, Sep. 9-11, 2014.
Geffrey et al., "Cannabidiol (CBD) Treatment for Refractory Epilepsy in Tuberous Sclerosis Complex," American Epilepsy Society, Annual General Meeting, Abstract, accessed on Jun. 23, 2015; https://www.aesnet.org/meetings_events/annual_meeting_abstracts/view/1868979, 2 pages.
Gedde et al., "Clinical Experience with Cannabis in Treatment-Resistant Pediatric Epilepsy," http://www.theroc.us/images/gedde.presentation.pdf, Sep. 9-11, 2014.
Geffrey et al., "Drug-drug interaction between clobazam and cannabidiol in children with refractory epilepsy," Epilepsia, 56(8):1246-1251 (2015).

Green, "CBD: An Unconventional Therapy," available online at http://nugs.com/article/cbd-an¬unconventional-therapy.html, published Mar. 24, 2014, 5 pages.
Gresham, et al., "Treating Lennox-Gastaut syndrome in epileptic pediatric patients with third generation rufinamide," Neuropsychiatr Dis Treat., 6:639-645 (2010).
Gross, et al., "Marijuana use and epilepsy: prevalence in patients of a tertiary care epilepsy center," Neurology, 62(11 ):2095-7 (2004).
Guerrini, et al., "Lamotrigine and Seizure Aggravation in Severe Myoclonic Epilepsy," Epilepsia, 39(5):508-512 (1998).
Guimaraes, et al., "Antianxiety effect of cannabidiol in the elevated plus-maze," Psychopharmacology (Berl)., 100(4):558-9 (1990); doi: 10.1007/BF02244012.
Goodman & Gilman, The Pharmacological Basis of Therapeutics (Brunton, Laurence L; Lazo, John S.; Parker, Keith, eds. (2006); New York: McGraw-Hill. ISBN 0-07-142280-3); Chapter 19, Pharmacotherapy of the Epilepsies.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL https://www.gwpharm.com/about-us/news/gw-pharmaceuticals-announces-epidiolex%C2%AE-receives-fast-track-designation-fda-treatment.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, 8 pages.
GWPharm [online], "GW Pharmaceuticals Provides Update on Orphan Program in Childhood Epilepsy for Epidiolex®," GW Pharmaceuticals Press Release, Nov. 15, 2013, 5 pages.
GWPharm [online], "Orphan Drug Designation Granted for Epidiolex in Dravet syndrome by the FDA-Seven Expanded Access INDs granted by FDA to US physicians to treat with Epidiolex 125 children suffering from intractable epilepsy syndromes," GW Pharmaceuticals Press Release, Nov. 15, 2013, 5 pages.
GWPharm [online], "GW Pharmaceuticals Announces Preliminary Results of Phase 2a Study for its Pipeline Compound GWP42006," GW Pharmaceuticals Press Release, Feb. 21, 2018, 5 pages.
Heinemann, et al., "An Overview of in Vitro Seizure Models in Acute and Organotypic Slices," Chapter 4, 35-44 (2006).
Hess et al., "Cannabidiol as a new treatment for drug-resistant epilepsy in tuberous sclerosis complex," Epilepsia, 57(10):1617-1624 (2016).
Hill, et al., "Δ9-Tetrahydrocannabivarin suppresses in vitro epileptiform and in vivo seizure activity in adult rats." Epilepsia, 51(8):1522-32 (2010); doi: 10.1111/j.1528-1167.2010.02523.x. Epub Feb. 26, 2010.
Hill et al., "Cannabidivarin is anticonvulsant in mouse and rat," Br. J Pharmacol, 167(8):1629-1642 (2012).
Holmes, et al., "Choosing the correct AED: From Animal Studies to the Clinic," Pediatr Neurol. 38(3):151-162 (2008).
Iannotti, et al., "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability," ACS Chem Neurosci., 5(11):1131-41 (2014); doi: 10.1021/cn5000524.
*Insys Development Company, Inc.* v. *Gw Pharma Limited and Otsuka Pharmaceutical Co., Ltd.*, Decision in IPR2017-00503, U.S. Pat. No. 9,066,920, dated Jul. 7, 2017, 26 pages.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.
*Insys Development Company, Inc.* v. *GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.

(56) References Cited

OTHER PUBLICATIONS

*Insys Development Company, Inc.* v. *GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.

*Insys Development Company, Inc.* v. *GW Pharma Limited and Otsuka Pharmaceutical Co., Ltd.*, Deposition of H. Steve White, dated Dec. 13, 2016, 50 pages.

*Insys Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.

*Insys Development Company, Inc.* v. *GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.

*Insys Development Company, Inc.* v. *GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.

*Insys Development Company, Inc.* v. *GW Pharma Limited and Otsuka Pharmaceutical Co., Ltd.*, Petitioner's Reply to Response in IPR2017-00503, U.S. Pat. No. 9,066,920, dated Jan. 19, 2018.

International Preliminary Report on Patentability in International Application No. PCT/GB2010/051066, dated May 3, 2011.

International Preliminary Report on Patentability for International Application No. PCT/GB2015/053030, dated Apr. 18, 2017.

International Preliminary Report on Patentability for International Application No. PCT/GB2012/052284, dated Mar. 29, 2014.

International Preliminary Report on Patentability for International Application No. PCT/GB2015/051775, dated Aug. 10, 2016.

International Preliminary Report on Patentability for International Application No. PCT/US2017/050868, dated Oct. 11, 2018, 7 pages.

International Search Report and Written Opinion for International Application No. PCT/US2017/050868, dated Aug. 6, 2017, 14 pages.

International Search Report and Written Opinion for International Application No. PCT/US2017/051943, dated Sep. 12, 2017, 10 pages.

International Search Report and Written Opinion for International Application No. PCT/GB2017/051914, dated Sep. 12, 2017.

International Search Report and Written Opinion for International Application No. PCT/GB2015/051775, dated Dec. 23, 2015.

International Search Report and Written Opinion for International Application No. PCT/GB2015/051066, dated Jan. 1, 2012.

International Search Report and Written Opinion for International Application No. PCT/GB2011/050649, dated Sep. 30, 2012.

International Search Report and Written Opinion dated Nov. 16, 2012 for International Application No. PCT/GB2012/052284, dated Mar. 29, 2014.

International Search Report for International Application No. PCT/GB2010/051066, dated Jan. 6, 2011.

International Search Report for International Application No. PCT/GB2012/050002, dated Jul. 12, 2012.

International Preliminary Report on Patentability dated Dec. 12, 2013 for International Application No. PCT/GB2012/052284.

International Preliminary Report on Patentability dated Jun. 9, 2011 for International Application No. PCT/GB2010/051066.

International Preliminary Report on Patentability dated Sep. 1, 2017 for International Application No. PCT/GB2016/051792.

International Search Report and Written Opinion dated Aug. 25, 2015 for International Application No. PCT/GB2015/051776.

International Search Report and Written Opinion dated Aug. 26, 2015 for International Application No. PCT/GB2015/051775.

International Search Report and Written Opinion dated Dec. 13, 2010 for International Application No. PCT/GB2010/051066.

International Search Report and Written Opinion dated May 30, 2011 for International Application No. PCT/GB2011/050649.

International Search Report dated Nov. 16, 2010 for International Application No. PCT/GB2010/051066.

International Search Report dated Feb. 24, 2012 for International Application No. PCT/GB2012/050002.

International Search Report and Written Opinion dated Oct. 25, 2016 for International Application No. PCT/GB2016/052340, 12 pages.

IUPHAR/BPS Guide to Pharmacology [online], "Entry for Δ 9-tetrahydrocannabidiol," available on or before Mar. 29, 2016, retrieved on Jun. 20, 2018, URL <http://www.guidetopharmacology.org/GRAC/LigandDisplayForward?tab=biology&ligandID=242>, 2 pages.

Iuvone, et al., "Neuroprotective effect of cannabidiol, a non-psychoactive component from Cannabis sativa, on beta-amyloid-induced toxicity in PC12 cells," J Neurochem., 89(1): 134-41 (2004).

Izzo, et al., "Non-psychotropic plant cannabinoids: new therapeutic opportunities from an ancient herb," Trends in Pharmacological Sciences, 30(10):515-527 (2009).

Jacobson, "Survey of Current Cannabidiol Use in Pediatric Treatment-Resistant Epilepsy," Apr. 22, 2013; https://www.thcint.eom/uploads/1/9/3/7/19371199/cannabidiol_use_in_pediatric_epilepsy.pdf, 1 page.

Jeavons, et al., "Sodium valproate in treatment of epilepsy," Br Med J., 2(5919):584-6 (1974).

Jones et al. [online], Info & Metrics / Article Information,"Cannabidiol Displays Antiepileptic from and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.

Joy, et al., "Marijuana and Medicine. Assessing the Science Base," National Academy Press. Washington D.C., 1999, 170 pages.

Jutras-Aswad, Didier, M.D., M.S. of the Department of Psychiatry for the University of Montreal presents his talk on "CBD in Animal Models and Human Trials of Opiate Abuse," at NYU School of Medicine's Cannabidiol Conference (Oct. 4, 2013). Video published online, <http://faces.med.nyu.edu/research-education/cannabidiol-conference>.

Kahan, et al., "Risk of selection bias in randomized trials," Trials, 16:405 (2015).

Karler, et al., "The cannabinoids as potential antiepileptics," J Clin Pharmacol, 21(8-9 Suppl):437S-447S (1981).

Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.

Katz, Russell ("Rusty"), M.D. former Director of the Division of Neurology Products at the FDA presents his talk on "Dravet and Lennox-Gastaut Syndromes: The Orphan Drug Process," at NYU School of Medicine's Cannabidiol Conference (Oct. 4, 2013). Video published online, <http://faces.med.nyu.edu/research-education/cannabidiol-conference>.

Khan et al., "Key Attributes of TKDL: Laooq-e-Quinnab/Barai Zeequn-Nafs," Khazaain-al-Advia, 1911 (with English translation), 2 pages.

Khan et al., Key Attributes of TKDL: Nushka-e-Qutoor, Muheet-e-Azam, 1887 (with English translation), 2 pages.

Khan et al., "Key Attributes of TKDL: Sufoof-e-Qinnab Barae Waja," Khazaain-al-Adiva, 1911, (with English translation), 5 pages.

Khan et al., "Key Attributes of TKDL: Usaara-e-Qinnab Barai Qoolanj," Khazaain-al-Advia, 1911 (with English translation), 6 pages.

Khan et al., "Key Attributes of TKDL: Zimad-e-Qinnab," Khazaain-al-Adiva, 1911 (with English translation), 5 pages.

Kelley, et al., "Doose syndrome (myoclonic-astatic epilepsy): 40 years of progress," Developmental Medicine & Child Neurology, 52:988-993 (2010).

Klitgaard, et al., "Electrophysiological, neurochemical and regional effects of levetiracetam in the rat pilocarpine model of temporal lobe epilepsy," Seizure, 12(2):92-100 (2003).

Klitgaard, et al., "Evidence for a unique profile of levetiracetam in rodent models of seizures and epilepsy," European Journal of Pharmacology, 353(2):191-206 (1998).

Kramer, et al., "Febrile infection-related epilepsy syndrome (FIRES): pathogenesis, treatment, and outcome: a multicenter study on 77

(56) References Cited

OTHER PUBLICATIONS children," Epilepsia, 52(11):1956-65 (2011); doi:10.1111/j.1528-1167.2011.03250.x. Epub Aug. 29, 2011.
Kwan et al., "Definition of drug resistant epilepsy: consensus proposal by the ad hoc Task Force of the ILAE Commission on Therapeutic Strategies," Epilepsia, 51(6):1069-77 (2010); doi:10.1111/j.1528-1167.2009.02397.x. Epub Nov. 3, 2009. Erratum in: Epilepsia. Sep. 2010;51(9): 1922.
LeafScience.com [online], "What are the Highest CBD Strains?" Oct. 15, 2014, retrieved on Feb. 16, 2017, URL www.leafscience.com/2014/10/15/highest-cbd-strains/.
Leo, et al., "Cannabidiol and epilepsy: Rationale and therapeutic potential," Pharmacological Research, 107:85-92 (2017).
Letter from Opponent Regarding Oral Proceedings for European Patent No. EP2448637, dated Oct. 20, 2016, 6 pages.
Lewis, "Mystery Mechanisms," The Scientist.com, Jul. 29, 2016, retrieved on Nov. 8, 2017, 2 pages.
Lieu, et al., "Assessment of self-selection bias in a pediatric unilateral hearing loss study," Otolaryngol Head Neck Surg. ,142(3):427-433 (2010).
Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).
Long, et al., "The pharmacological actions of cannabidiol," Drugs of the Future, 30(7):747-53 (2005).
Loscher and Schmidt, "Modern antiepileptic drug development has failed to deliver: ways out of the current dilemma," Epilepsia, 52(4):657-78 (2011); doi: 10.1111/j.1528-1167.2011.03024.x.
Lutz, "On-demand activation of the endocannabinoid system in the control of neuronal excitability and epileptiform seizures," Biochem Pharmacol., 68(9):1691-8 (2004).
Lowenstein, "Chapter 363: Seizures and Epilepsy," Diseases of the Central Nervous System, 2498-2512 (2008).
Luttjohann, et al., "A revised Racine's scale for PTZ-induced seizures in rats," Physiol Behav., 98(5):579-86 (2009); doi:10.1016/j.physbeh.2009.09.005.
Maa et al., "The case for medical marijuana in epilepsy," Epilepsia, 55(6):783-786 (2014).
Mackie, "Cannabinoid receptors as therapeutic targets," Annu Rev Pharmacol Toxicol., 46:101-22 (2006).
Majoosi, et al. Kaamil-al-Sena'ah, Part II, Central Council for Research in Unani Medicine. 2005:116. Arabic. Exhibit 2.
Malfait, et al. "The nonpsychoactive cannabis constituent cannabidiol is an oral anti-arthritic therapeutic in murine collagen-induced arthritis," PNAS, 97(17):9561-9566 (2000).
Manno, "Status Epilepticus: Current Treatment Strategies," The Neurohospitalist, 1(1):23-31 (2011).
Mattson, et al., "Comparison of carbamazepine, phenobarbital, phenytoin, and primidone in partial and secondarily generalized tonic-clonic seizures," N. Engl. J. Med, 313(3):145-151 (1985).
Mattson, et al., "Prognosis for total control of complex partial and secondary generalized tonic clonic seizures," Neurology, 47:68-76 (1996).
MARINOL Label retrieved from https://www.accessdata.fda.gov/drugsatfda_docs/label/2006/018651s025s026lbl.pdf.
Martin et al., "Structure-Anticonvulsant Activity Relationships of Cannabidiol Analogs," National Institute on Drug Abuse, Research Monograph Series, 79:48-58 (1987).
McCormick et al., "On the cellular and network bases of epileptic seizures," Annu Rev Physiol., 63:815-46 (2001).
McNamara, "Chapter 19: Pharmacotherapy of the Epilepsies,", Goodman & Gilman's The Pharmacological Basis of Therapeutics 11th ed., McGraw-Hill Companies, pp. 501-525 (2006).
Mechoulam, et al., "Cannabidiol: An Overview of Some Pharmacological Aspects," J Clin Pharmacol, 42:11S-19S (2002).
Mechoulam, et al., Toward drugs derived from cannabis, Naturwissenschaften, 65(4):174-9 (1978).
Merlis, "Proposal for an international classification of the epilepsies," Epilepsia, 1(1):114-9 (1970).

Miller, et al., "Mapping genetic modifiers of survival in a mouse model of Dravet syndrome," Genes, Brain and Behavior, 13:163-172 (2014).
Models of Chemically-Induced Acute Seizures 127-152, 2006.
Montouris, "Rational approach to treatment options for Lennox-Gastaut syndrome," Epilepsia, 52:10-20 (2011).
Morard, et al., "Conversion to Sirolimus-Based Immunosuppression in Maintenance Liver Transplantation Patients," Liver Transplantation, 13:658-664 (2007).
Moral, et al., "Pipeline on the Move," Drugs of the Future, 39(1):49-56 (2014).
Ng et al., "Illicit drug use and the risk of new-onset seizures." Am J Epidemiol., 132(1):47-57 (1990).
Neto, et al., "The role of polar phytocomplexes on anticonvulsant effects of leaf extracts of Lippia Alba (Mill.) N.E. Brown chemotypes," J. Pharm Pharmacol. 61(7):933-9 (2009).
Notice of Allowance in U.S. Appl. No. 13/380,305, dated Dec. 10, 2014.
Notice of Allowance in U.S. Appl. No. 13/380,305, dated Mar. 19, 2015.
Notice of Appeal in European Patent No. EP2448637, dated Feb. 14, 2017.
Notice of Opposition to a European Patent No. EP2448637, Dated Dec. 5, 2014.
Oakley, et al., "Dravet Syndrome Insights into pathophysiology and therapy from a mouse model of Dravet syndrome," Epilepsia 52(Suppl. 2):59-61 (2011).
Obay et al., "Antiepileptic effects of ghrelin on pentylenetetrazol-induced seizures in rats," Peptides, 28(6):1214-9 (2007). Epub Apr. 19, 2007.
Office Action in U.S. Appl. No. 13/380,305, dated Aug. 25, 2014.
Opponent Response to the Preliminary Opinion of the Opposition Division in European Patent No. EP2448637, dated Jun. 23, 2016.
Opponent Response dated to Sep. 9, Preliminary 2016, 25 Opinion pages of the Opposition Division in European Patent No. EP2448637, dated Sep. 9, 2016.
Opponent Response to the Written Submissions in European Patent No. EP2448637, dated Oct. 12, 2016.
Opponent Response to the Written Submissions in European Patent No. EP2448637, dated Oct. 20, 2016.
Opponent Response to the Written Submissions in European Patent No. EP2448637, dated Nov. 4, 2016.
Patent Owners' Preliminary Response for IPR2017-00503 dated Apr. 11, 2017.
PCT International Preliminary Reporton Patentability in International Appln. No. PCT/US2017/050868, dated Jun. 18, 2019.
PCT International Search Report and Written Opinion in International Appln. No. PCT/US2017/050868, dated Jun. 21, 2018.
Pelliccia, et al., "Treatment with CBD in oily solution of drug-resistant paediatric epilepsies," Available online Sep. 2, 2010, Retrieved Jun. 30, 2015; http://www.gwpharm.com/uploads/pelliccia-2002-treatmentwithcbdinoilysolutionofdrug-resistantpediatricepilepsies.pdf.
Pereira, et al., "Study pharmacologic of the GABAergic and glutamatergic drugs on seizures and status epilepticus induced by pilocarpine in adult Wistar rats," Neurosci Lett., 419(3):253-7 (2007). Epub Apr. 13, 2007.
Perucca, "Cannabinoids in the Treatment of Epilepsy: Hard Evidence at Last?" Journal of Epilepsy Research, 7(2):61-76 (2017).
Pertwee, "Cannabinoid receptor ligands: clinical and neuropharmacological considerations, relevant to future drug discovery and development," Expert Opin Investig Drugs, 9(7):1553-71 (2000).
Pertwee, "The diverse CB1 and CB2 receptors pharmacology of three plant cannabinoids: Alpha9 Tetrahydrocannabinol, cannabidiol and alpha9-tetrahydrocannabivarin," Br. J. Pharmacol., 153(2):199-215 (2008).
Pertwee, "The Pharmacology and Therapeutic Potential of Cannabidiol," Cannabinoids, Chapter 3, DiMarzo, V. (Ed.), pp. 32-83 (2004).
Petition for Inter Partes Review U.S. Pat. No. 9, 066,920 dates Dec. 16, 2016.

(56) References Cited

OTHER PUBLICATIONS

Petitioner's Reply to Patent Owner's Response in Inter Partes Review No. IPR2017-00503, filed Jan. 19, 2018.
Petrocellis, et al., "Effects of cannabinoids and cannabinoid-enriched Cannabis extracts on TRP channels and endocannabinoid metabolic enzymes," British Journal of Pharmacology, 163:1479-1494 (2011).
Pohl, et al., "Effects of flunarizine on Metrazol-induced seizures in developing rats," Epilepsy Res., 1(5):302-5 (1987).
Porter et al., "Report of a parent survey of cannabidiol-enriched cannabis use in pediatric treatment-resistant epilepsy," Epilepsy Behav., 29(3):574-577 (2013).
Potter, "Cannabis Horticulture," Chapter 4, Handbook of Cannabis, ed. Roger G. Pertwee, pp. 65-88 (2014).
Poortman-Van Der Meer, "A contribution to the improvement of accuracy in the quantitation of THC," Forensic Science International, Apr. 1999, 101(1):1-8.
Pouton, "Lipid formulations for oral administration of drugs: non-emulsifying, self-emulsifying and 'self-micro emulsifying' drug delivery systems," Eur J Pharm Sci, 11(Suppl. 2):S93-S98 (2000).
Press, et al., "Parental reporting of response to oral cannabis extracts for treatment of refractory epilepsy," Epilepsy Behav. Apr. 2015;45:49-52. doi: 10.1016/j.yebeh.2015.02.043. Epub Apr. 3, 2015.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani, et al. "Epilepsy in Aicardi—Goutieres syndrome," Official J Eur Paediatric Neurology Society, 18:30-37 (2014).
Rauca, et al. "The role of superoxide dismutase and alpha-tocopherol in the development of seizures and kindling induced by pentylenetetrazol—influence of the radical scavenger alpha-phenyl-N-tert-butyl nitrone," Brain Res. May 29, 2004;1009(1-2):203-12.
Resstel et al., "5-HT1A receptors are involved in the cannabidiol-induced attenuation of behavioural and cardiovascular responses to acute restraint stress in rats," Br J Pharmacol. Jan. 2009; 156(1): 181-8.
Reply of the Patent Proprietor to the Notice(s) of Opposition in European Patent No. 2448637, dated May 28, 2015, 12 pages.
Reply to Communication from the examining Division in European Patent Application No. 10734541.5 dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016, 13 pages.
Reply to Opponent's Written Submission in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in U.S. Appl. No. 13/380,305, filed Mar. 2, 2015, 3 pages.
Rohrback, Brian G., Ph.D, MBA President of Infometrix, Inc. presents his talk on "Assays of Cannabinoids," at NYU School of Medicine's Cannabidiol Conference (Oct. 4, 2013). Video published online, <http://faces.med.nyu.edu/research-education/cannabidiol-conference>.
Rosenberg et al., "Cannabinoids and Epilepsy," Neurotherapeutics, 12(4):747-768 (2015).
Russo, "Taming THC: potential cannabis synergy and phytocannabinoid-termoid entourage effects," British J. of Pharm. 1333 (2011).
Rubio, et al. "In vivo Experimental Models of Epilepsy," Central Nervous System Agents in Medicinal Chemistry, 10:298-309, 2010.
Sadanandasarma et al., Rasatarangini. 11th Ed. 1979:720-3. Sanskrit.
Sander, "The epidemiology of epilepsy revisited." Curr Opin Neural. Apr. 2003; 16(2): 165-70.
Sastri et al., Anandakandam. 1st Edition. 1952:241. Sanskrit.
Screenshot confirming date of Epidiolex (Cannabidiol) in Treatment Resistant Epilepsy, Apr. 2015; https://epilepsyontario.org/wp-content/uploads/2015/Epidiolex-Cannabidiol-in-Treatment-Resistant-Epilepsy AAN-POSTER 08Apr2015.pdf, 1 page.
Scuderi et al., "Cannabidiol in medicine: a review of its therapeutic potential in CNS disorders," Phytother Res., 23(5):597-602 (2009).
Shukla, [online], "New Automated Purification Strategies for Scale-Up," PCISynthesis.com, posted Dec. 25, 2017, https://www.pcisynthesis.com/new-automated-purification-strategies-for-scale-up/, 5 pages.
Silva et al., "Position Statement on the Use of Medical Cannabis for the Treatment of Epilepsy in Canada," Can J. Neurol. Sci., 33:783-786 (2006).
Smith, R. M., "Identification of Butyl Cannabinoids in Marijuana," Journal of Forensic Sciences, 42:610-618 (1997).
Sperling et al., "Carisbamate as adjunctive treatment of partial onset seizures in adults in two randomized, placebo-controlled trials," Epilepsia, 51(3):333-343 (2010).
Stafstrom et al., "Models of Pediatric Epilepsies: Strategies and Opportunities," Epilepsia, 47(8):1407-1414(2006).
Statement of Opposition for EP10734541.5, mailed Decembers, 2014.
Statement of Grounds of Appeal for European Application No. 10734541.5 in the name of GW Pharma and Otsuka Pharmaceutical Co. Limited Appellant/Opponent: Insys Therapeutics Inc., dated Apr. 21, 2017.
Statement of Grounds of Appeal for European Application No. 10734541.5 on behalf of the Proprietors: GW Pharma Limited and Otsuka Pharmaceutical CO Limited, dated Apr. 12, 2017.
Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 140:83-93 (2004).
Study NCT02224690—A Study to Investigate the Efficacy and Safety of Cannabidiol (*GWP42003-P; CBD*) AS Adjunctive Treatment for Seizures Associated With Lennox-Gastaut Syndrome in Children and Adults, Aug. 22, 2014; https://clinicaltrials.gov/ct2/show/NCT02224690,1 page.
Supplemental Expert Statement of Professor Benjamin J. Whalley, dated Nov. 4, 2016, 9 pages.
Swann et al., The effects of seizures on the connectivity and circuitry of the developing brain. Ment Retard Dev Disabil Res Rev. 2004; 10(2):96-100.
Tanya Lewis, Mystery Mechanisms, The Scientist Magazine, Jul. 29, 2016.
Third Party Observations for Application No. AU20 I 2314128, mailed Mar. 19, 2015.
Third Party Observations for Application No. EP10734541.5, mailed Apr. 3, 2017.
Third Party Observations for Application No. EP1712658.1, mailed Nov. 22, 2013.
Third Preliminary Amendment under 37 C.F.R. 1.115 for U.S. Appl. No. 13/380,305, dated May 23, 2014, 4 pages.
Thomas et al., "Evidence that the plant cannabinoid Delta9-tetrahydrocannabivarin is a cannabinoid CBI and CB2 receptor antagonist," Br J Pharmacol., 146(7):917-926 (2005).
Thurman et al., "Standards for epidemiologic studies and surveillance of epilepsy," Epilepsia, 52 (Suppl 7):2-26 (2011).
Thumma et al., "Influence of plasticizers on the stability and release of a prodrug of ./19-tetrahydrocannabinol incorporated in poly (ethylene oxide) matrices," Eur J Pharmaceutics and Biopharmaceutics, 70(2):605-614 (2008).
Thurstone, "Avoid Charlotte's Web for Epilepsy," Jun. 26, 2014, URL <http://drthurstone.com/charlotted-web-not-safest-option-epilepsy-treatment/>, 4 pages.
Transcript of Dr. H. Steven White's deposition, dated Dec. 29, 2017.
Trembly & Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract only.
Turkanis et al., "An Electrophysiological Analysis of the Anticonvulsant Action of Cannabidiol on Limbic Seizures in Conscious Rats," Epilepsia., 20:351-363 (1979).
Usami et al., "Synthesis and pharmacological evaluation in mice of halogenated cannabidiol derivatives," Chem Pharm Bull (Tokyo), 47(11):1641-1645 (1999).

(56) References Cited

OTHER PUBLICATIONS

Unimed Pharmaceuticals, Inc., "Marinol®," Jul. 2006 <https://www.accessdata.fda.gov/dmgsatfdadocs/label/2006/018651 s025s026lbl.pdf>, 11 pages.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jun. 21, 2017, 6 pages.
USPTO Information Disclosure Statement Form PTO-1449 for U.S. Appl. No. 13/380,305, dated Nov. 24, 2014, 8 pages.
Utah.gov [online], "2nd Agenda Controlled Substances Advisory Committee Meeting," Nov. 12, 2013, URL <httos://www.utah.gov/pmn/files/81459.pdt>, 63 pages.
Van Rijckevorsel, "Treatment of Lennox-Gastaut syndrome: overview and recent findings," Neuropsychiatr Dis Treat. Dec. 2008; 4(6): 1001-1019.
Van Straten et al., "Update on the Management of Lennox-Gastaut Syndrome," Pediatric Neurology, 47:153-161 (2012).
Velisek, "Models of Chemically-Induced Acute Seizures," Models Seizure Epilepsy, 127-152 (2006).
Veliskova, Chapter 48 "Behavioral Characterization of Seizures in Rates," Model Seizures Epilepsy, 601-611 (2006).
Vollner et al., Haschisch XX: Cannabidivarin, ein neuer Haschisch-Inhaltsstoff. Tetrahedron Lett. 1969;10(3):145-7.
Wahle et al., "Development of tolerance to the anticonvulsant effect of valproate but not to ethosuximide in a rat model of absence epilepsy," Eur J Pharma. May 1990; 181(1-2):1-8.
Wallace et al., "Pharmacotherapy for Dravet Syndrome," Pediatr. Drugs, 18:197-208 (2016).
Wallace et al., "Assessment of the role of CB 1 receptors in cannabinoid anticonvulsant effects," Eur J Pharmacol. Sep. 28, 2001;428(1):51-7.
Weston et al., "Tetrahydrocannabivarin exhibits anticonvulsant effects in a piriform cortical brain slice model of epileptiform activity." Pro British Pharm Soc 75th Anniv Meeting. Dec. 31, 2006 Found on: http://www.pA2online.org/abstract/abstract.jsp?abid=28533. Abstract Only. 1 Page.
Whalley, Benjamin J. Ph.D. of the University of Reading presents his talk on "Cannabis and Epilepsy: Cannabidiol (CBD) and Cannabidavarin (CBDV) in Preclinical Models of Seizure and Epilepsy," at NYU School of Medicine's Cannabidiol Conference (Oct. 4, 2013). Video published online. <http://faces.med.nyu.edu/research-education/cannabidiol-conference>.
"When to Expect Results from CW Hemp Oil", downloaded Sep. 5, 2017, https://www.cwhemp.com/blog/expecting-results-from-hemp.
Wikipedia.org [online], "Cannabinoid," Wikipedia, Apr. 2003, retrieved on Mar. 1, 2017, URL <https://en.wikipedia.org/wiki/Cannabinoid>, 15 pages.
Williams, "The Key to Healing Broken Bones May be Found in This Illegal Drug," Jul. 25, 2015; https://www.fool.com/investing/high-growth/2015/07/25/the-key-to-healing-broken-bones-may-be-found-in-th.aspx#:~:text=As%20published%20in%20the%20Journal,rats%20in%20just%20eight%20 weeks, 5 pages.
Wingerchuk, "Cannabis for medical purposes: cultivating science, weeding out the fiction," Lancet. Jul. 24-30, 2004;364(9431):315-6.
Wright et al., Cannabidiol (CBD) in Dravet Syndrome: A Randomised, Dose-Ranging Pharmacokinetics and Safety Trial (GWPCARE1), Epilepsia, 58(Suppl. 5):S5-S199 (2017), p. 0240 Abstract, 1 page.
Written Opinion for International Application No. PCT/GB2010/0051066, dated Nov. 22, 2010, 4 pages.
Yu et al., "Reduced sodium current in GABAergic interneurons in a mouse model of severe myoclonic epilepsy in infancy," Nature Neuroscience, 9(9):1142-1149 (2006).
Yuriev, "Endogenic cannabinoid system is a new perspective object of pharmacotherapeutic effect to disease of nervous system," Ukrainsky Metodichny Chasopis, 6(50):21-29 (2005) (with English Abstract).
Zhao et al., "Chapter 27: Repetitive Seizures in the Immature Brain," Models of Seizures and E[epilepsy, 341-350 (2006).
Zuardi et al., "Cannabidiol, a Cannabis sativa constituent, as an antipsychotic drug," Braz J Med Biol Res., 39(4):421-429 (2006).
Zuardi et al., "Cannabidiol: from an inactive cannabinoid to a drug with wide spectrum of action," Rev Bras Psiquiatr, 30(3):271-280 (2008).
Akiyama, M. et al., "Dravet Syndrome:A Genetic Epileptic Disorder," Acta. Med. Okayama, 66(5):369-376 (2012).
Bergamaschi, M. M. et al., "Safety and Side Effects of Cannabidiol, a Cannabis sativa Constituent," Current Drug Safety, 6:237-249 (2011).
Carvill, G. L. et al., "GABRA1 and STXBP1: Novel generic causes of Dravet Syndrome," Neurology, 82:1245-1253 (2014).
Chiron, S., "Stiripentol for the treatment of Dravet syndrome," Orphan Drugs: Research and Reviews, 4:29-38 (2014).
Cilio, M. R. et al., "The case for assessing cannabidiol I epilepsy," Epilepsia, 55(6):787-790 (2014).
Clinical trials.gov [online], Identifier: NCT02224690. A Study to Investigate the Efficacy and Safety of Cannabidiol (GWP42003-P; CBD) as Adjunctive Treatment for Seizures Associated With Lennox-Gastaut Syndrome in Children and Adults (GWPCARE4) Jazz Pharmaceuticals, U.S. National Library of Medicine, last update posted Sep. 8, 2022, 3 pages; Retrieved from https://clinicaltrials.gov/ct2/show/NCT02224690.
Collins, T. R., Collins TR. What Neurologists are Doing About Medical Marijuana?, Neurology Today, Apr. 17, 2014, vol. 4, issue 8, 8 pages.
Crumrine, P. K., "Management of Seizures in Lennox-Gastaut Syndrome," Pediatr Drugs, 13(2):107-118 (2011).
Diacomit™ Product Monograph, Submission Control 142417, Date of Preparation, Dec. 19, 2012, 37 pages.
Gedde et al., "3.330 Whole Cannabis Extract of High Concentration Cannaboidol May Calm Seizures in Highly Refractory Pediatric Epilepsies," American Epilepsy Society, Dec. 2013, pp. 449-1450.
Hillig, K. W. & Mahlberg, P. G., "A chemotaxonomic analysis of cannabinoid variation in Cannabis (Cannabaceae)," American Journal of Botany, 91(6):966-975 (2004).
Jiang, R. et al., "Cannabidiol Is a Potent Inhibitor of the Catalytic Activity of Cytochrome P450 2C19," Drug Metab. Pharmacokinet., 28(4):332-338 (2013).
Jones, N. A. et al., "Cannabidiol exerts anti-convulsant effects in animal models of temporal lobe and partial seizures," Seizure, 21:344-352 (2012).
Kalepu, S. et al., "Oral lipid-based drug delivery systems—an overview," Acta Pharmaceutica Sinica B., 3(6):361-372 (2013).
Leahy, J. T. et al., "Clobazam as an adjunctive therapy in treating seizures associated with Lennox-Gastaut syndrome," Neuropsychiatric Disease and Treatment, 7:673-681 (2011).
Marinol® Product Description, NDA 18-651/S-025 and S-026, Jul. 2006, pp. 3-13.
Onfi™ (clobazam) tablets Prescribing Information, NDA 202067 Onfi (clobazam) Tablets for oral use FDA Approved Labeling Text, dated Oct. 21, 2011, 28 pages.
Oguni, H. et al., "Long-Term Prognosis of Lennox-Gastaut Syndrome," Epilepsia, 37(Suppl 3):44-47 (1996).
"Pot or not? Why parents of kids with epilepsy want access to marijuana treatment," CTVNews.ca Staff, Published Thursday, Jul. 18, 2013; Last Updated Thursday, Jul. 18, 2013, 2 pages; https://www.ctvnews.ca/health/health-headlines/pot-or-not-why-parents-of-kids-with-epilepsy-want-access-to-marijuana-treatment-1.1372695?cache=.
Saade, D. & Joshi, C., "Pure Cannabidiol in the Treatment of Malignant Migrating Partial Seizures in Infancy: A Case Report," Pediatric Neurology, 52:544-547 (2015); http://dx.doi.org/10.1016/j.pediatrneurol.2015.02.008.
Schafroth, M. A. et al., "Sterodivergent Total Synthesis of Δ9-Tetrahydrocannabinols," Angew. Chem. Int. Ed., 53:13898-13901 (2014).
Scheffer, I. E., "Diagnosis and long-term course of Dravet syndrome," Eur J of Paediatric Neurology 16 (2012) S5-S8.
Silva, R. et al., "Clobazam as Add-on Therapy in Children with Epileptic Encephalopathy," Can. J. Neurol. Sci., 33:209-213 (2006).
Smith, R. M. & Kempfert, K. D., "Δ1-3,4-CIS-Tetrahydrocannabinol in Cannabis Sativa," Phytochemistry, 16:1088-1089 (1977).

(56) References Cited

OTHER PUBLICATIONS

"University of Utah doctors: Say 'yes' to cannabis oil for kids," By Kirsten Stewart The Salt Lake Tribune, Nov. 13, 2013, 4 pages.
Zhornitsky & Potvin, "Cannabidiol in Humans—The Quest for Therapeutic Targets," Pharmaceuticals, 5:529-552 (2012).
Vanstraten, A.F. et al., "Update on the Management of Lennox-Gastaut Syndrome," Pediatric Neurology, 47:153-161 (2012).
Adams, R. et al., "Isolation of Cannabinol, Cannabidiol and Quebrachitol from Red Oil of Minnesota Wild Hemp," J. Am. Chem. Soc. 1940, 62, 8, 2194-2196.
Approval Letter for NDA 210365 Epidiolex, Jun. 25, 2018, 12 pages.
Arzimanoglou et al., "All children who experience epileptic falls do not necessarily have Lennox-Gastaut syndrome . . . but many do," Epileptic Disord. 2011, 13: S3-S13 (2011).
[No Author Listed], "High Rollers Bet On Cannabidiol (CBD)—Medical Marijuana Patients Come Up Short," Mar. 3, 2013, 9 pages; https://www.420magazine.com/community/threads/high-rollers-bet-on-cannabidiol-cbd-%E2%80%94-medical-marijuana-patients-come-up-short.185325/.
[No Author Listed], "Selected Media Examples Of Pediatric Applications OfCannabidiol (CBD)," Jun. 30, 2013, 4 pages; https://www.420magazine.com/community/threads/selected-media-examples-of-pediatric-applications-of-cannabidiol-cbd.192155/.
Allen G., "Florida Bill Would Allow Medical Marijuana For Child Seizures," Jan. 16, 2014, retrieved from https://www.npr.org/sections/health-shots/2014/01/16/262481852/florida-bill-would-allow-marijuana-extract-for-child-seizures, 16 pages.
Amada, N. et al., "Cannabidivarin (CBDV) suppresses pentylenetetrazole (PTZ)-induced increases in epilepsy-related gene expression," 2013, PeerJ, 1:e214; 18 pages; http://dx.doi.org/10.7717/peerj.214.
Bell, J., "Treatment With CBD In Oily Solution Of Drug-Resistant Paediatric Epilepsies," Oct. 18, 2011, 3 pages; https://www.420magazine.com/community/threads/treatment-with-cbd-in-oily-solution-of-drug-resistant-paediatric-epilepsies.154896/.
Bienenstock, D., "A Comprehensive History of Marijuana's Epilepsy-Treating Compound, CBD," Jun. 2014, Vice Article, retrieved from https://www.vice.com/da/article/mv53yp/desperately-seeking-cbd, 17 pages.
Carlini, E. A. et al., "Letter: Cannabidiol and Cannabis sativa extract protect mice and rats against convulsive agents," J Pharm Pharmacol. Aug. 1973;25(8):664-5. doi: 10.1111/j.2042-7158.1973.tb10660.x.
Chu-Shore, C. J. et al., "The natural history of epilepsy in tuberous sclerosis complex," Epilepsia, 51(7):1236-1241, 2010; doi: 10.1111/j.1528-1167.2009.02474.
Clinical trials.gov [online], Identifier: NCT02091206, A Dose Ranging Pharmacokinetics and Safety Study of GWP42003-P in Children With Dravet Syndrome (GWPCARE1), Jazz Pharmaceuticals, U.S. National Library of Medicine, last update posted Sep. 28, 2022, 9 pages; Retrieved from https://clinicaltrials.gov/ct2/show/NCT02091206.
Clinical trials.gov [online], Identifier: NCT02006628, A study to compare the change in symptom severity in participants with schizophrenia or related psychotic disorderwhen treated with GWP42003 or placebo in conjunction with existing anti-psychotic therapy over a period of six weeks, Jazz Pharmaceuticals, U.S. National Library of Medicine, last update posted Sep. 28, 2022, 9 pages; Retrieved from https://clinicaltrials.gov/ct2/show/NCT02006628.
Clinical trials.gov [online], Identifier: NCT02091375, Antiepileptic Efficacy Study of GWP42003-P in Children and Young Adults WithDravet Syndrome (GWPCARE1), Jazz Pharmaceuticals, U.S. National Library of Medicine, last update posted Sep. 28, 2022, 40 pages; Retrieved from https://www.clinicaltrials.gov/ct2/show/NCT02091375.
Cotter, B., "Medicinal marijuana stops seizures, brings hope to little girl," The Gazette, Jun. 9, 2013, 8 pages; https://gazette.com/health/medicinal-marijuana-stops-seizures-brings-hope-to-a-little-girl/article_520b074e-5c46-5d75-af95-bdd060f4a8b9.html.
Cotterell, A., "How One Young Girl Could Change Idaho's Strict Marijuana Laws," Jun. 17, 2014; https://www.knkx.org/law/2014-06-19/how-one-young-girl-could-change-idahos-strict-marijuana-laws, 8 pages.
Curatolo, P. et al., "Management of epilepsy associated with tuberous sclerosis complex (TSC): Clinical recommendations," European Journal of Paediatric Neurology, 16:582-586 (2012).
Depakene (valproic acid) capsules and oral solution, CV, Prescribing Information, 1978, 54 pages; https://www.accessdata.fda.gov/drugsatfda_docs/label/2013/018081s056lbl.pdf.
Dilantin-125®, NDA 08762 Dilantin-125 (Phenytoin Oral Suspension, USP) FDA Approved Labeling Text dated Feb. 2013, 15 pages.
Dimarzo, V., Declaration Under 37 C.F.R. 1.132, dated Aug. 24, 2017, 21 pages.
Epilepsy Patients Flock to Colorado after Medical Pot Gives Them Hope, Nov. 18, 2013, CBS Colorado News, 4 pages.
Elsohly, M. & Gul, W., "Chemical constituents of marijuana: The complex mixture of natural cannabinoids," Life Sciences, 78:539-548 (2005).
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
FDA'S Guidance for Industry Q3A Impurities in New Drug Substances, Revision 2, Jun. 2008, 17 pages.
FDA Guideline for Submitting Supporting Documentation in Drug Applications for the Manufacture of Drug Substances, published in 1987, 20 pages.
Fernandez-Ruiz, J. et al., "Cannabidiol for neurodegenerative disorders: important new clinical applications for this phytocannabinoid?" British Journal of Pharmacology, 75(2):323-333 (2012).
Flatow, N., "How Medical Marijuana Is Giving a Six-Year-Old Boy New Life," Sep. 18, 2012, 2 pages; https://archive.thinkprogress.org/how-medical-marijuana-is-giving-a-six-year-old-boy-new-life-b5a486fb1d48/.
Gaoni, Y. & Mechoulam, R., "The Isolation and Structure of Δ1-Tetrahydrocannabinol and Other Neutral Cannabinoids from Hashish," J Am Chem Soc. Jan. 13, 1971;93(1):217-24. doi: 10.1021/ja00730a036.
Gaoni, Y. & Mechoulam, R., "Isolation, Structure, and Partial Synthesis of an Active Constituent of Hashish," J. Am. Chem. Soc. 1964, 86, 8, 1646-1647.
Garde, D., "GW Pharmaceuticals Announces Physician Reports of Epidiolex Treatment Effect in Children and Young Adults With Treatment-Resistant Epilepsy From Physician-Led Expanded Access Treatment Program," Jun. 17, 2014, 4 pages; https://www.fiercebiotech.com/biotech/gw-pharmaceuticals-announces-physician-reports-of-epidiolex-r-treatment-effect-children-and.
Geffrey, A. et al., "Cannabidiol (CBD) Treatment for Refractory Epilepsy in Tuberous Sclerosis Complex (TSC)," Dec. 4, 2014; www.aesnet.org, Abstract 2.427, 2 pages.
Gloss, D. & Vickrey, B., "Cannabinoids for epilepsy (Review)," Cochrane Database of Systematic Reviews 2014, Issue 3. Art. No. CD009270, 9 pages; DOI: 10.1002/14651858.CD009270.pub3.
Haller, S. & Carroll, I., "Medical marijuana for kids? Some praise results while others worry about risks," Jul. 9, 2013, 3 pages; https://www.nbcnews.com/healthmain/medical-marijuana-kids-some-praise-results-while-others-worry-about-6c10506407.
Hanus et al., "Phyto-cannabinoids: a unified critical inventory," Review Article, Natural Product Reports; Royal Society of Chemistry, vol. 33, No. 12, Dec. 2016, pp. 1347, 1448, 37 pages.
Hefler, J., "Parents of epileptic N.J. tot lament medical marijuana delays," The Philadelphia Enquirer, Jun. 22, 2013, 5 pages; https://www.inquirer.com/philly/health/20130623_Parents_of_epileptic_N_J_tot_lament_medical_marijuana_delays.html.
Hegde, M. et al., "Seizure exacerbation in two patients with focal epilepsy following marijuana cessation," Epilepsy & Behavior, 25:563-566 (2012).
Hill, A. J. et al., "Phytocannabinoids as novel therapeutic agents in CNS disorders," Pharmacology & Therapeutics, 133:79-97 (2012).
Holmes, G. L. et al., "Tuberous Sclerosis Complex and Epilepsy: Recent Developments and Future Challenges," Epilepsia, 48(4):617-630, 2007.

(56) References Cited

OTHER PUBLICATIONS

ICE Epilepsy Alliance, The Dravet Syndrome Spectrum, Nov. 2008, 2 pages.
Jacobson, C., "Treating Epilepsy with Pharmaceutical-Grade CBD", Cannabis Science Today, Podcast, 2023, transcript timeline 4 pages; https://agriculturalgenomics.org/podcast/season1/treating-epilepsy-with-pharmaceutical-grade-cbd/.
Jones, P. G. et al., "Cannabidiol," Acta Cryst., B33:3211-3214 (1977).
Kassai et al., "Severe Myoclonic epilepsy in Infancy: A Systematic Review and a Meta-Analysis of Individual Patient Data," Epilepsia, 49(2):343-348 (2008).
Kerr, D. N. S. & Pillai, P. M., "Clobazam as adjunctive treatment in refractory epilepsy," British Medical Journal, 286:1246-1247 (1983).
Kopka, M., "Cannabinoids in the treatment of epilepsy—an updated review," Journal of Epileptology, 2019, 27:35-42; 10.21307/jepil-2019-004.
Krasowski, M. D., "Antiepileptic Drugs. Therapeutic Drug Monitoring of the Newer Generation Drugs," Jun. 2013, Clinical Laboratory News, https://www.aacc.org/cln/articles/2013/june/antiepileptic-drugs, 6 pages.
Leonard, B. E., "Therapeutic Uses of Cannabis," British Medical Association (BMA). Harwood Academic Publishers, UK. 1997, pp. 592.
Loscher, W. & Rogawski, M. A., "How theories evolved concerning the mechanism of action of barbiturates," Epilepsia, 53(Suppl. 8):12-25, 2012; doi: 10.1111/epi.12025.
Marks, W. J. et al., "Management of Seizures and Epilepsy," Am Fam Physician. 1998;57(7):1589-1600.
Masangkay, E. G., "FDA Confirms GW Pharmaceuticals' IND For Epidiolex Trial In Dravet Syndrome," May 9, 2014, 2 pages.
Mechoulam, R. et al., "Cannabidiol—Recent Advances," Chemistry & Biodiversity, vol. 4, pp. 1678-1692 (2007).
Mechoulam, R., "Conversation with Ralph Mechoulam," Addiction Jun. 2007;102(6):887-93. doi: 10.1111/j.1360-0443.2007.01795.x.
Mechoulam, R. & Parker, L. A., "The Endocannabinoid System and the Brain," Annu. Rev. Psychol. 2013. 64:21-47.
Mechoulam, R. & Parker, L. A., "Towards a better cannabis drug," British Journal of Pharmacology (2013) 170 1363-1364.
Moore, Y. et al., "Cannabidiol reduced freguency of convulsive seizures in drug resistant Dravet Syndrome," Structured Abstracts of Sentinel Articles: Picket, first published Sep. 22, 2017, reported in Arch Dis Child Educ Pract Ed Oct. 2018, vol. 103, No. 5., 2 pages. Abstract.
New Drug Application No. 210365 for Epidiolex (cannabidiol) 100 mg/ml oral solution, Jun. 25, 2018, 12 pages.
[No Author Listed], The Reuters Staff, BRIEF-GW Pharma receives FDA fast-track designation for Dravet syndrome treatment, Jun. 6, 2014, 1 page; https://www.reuters.com/article/gwpharmaceuticals-brief/brief-gw-pharma-receives-fda-fast-track-designation-for-dravet-syndrome-treatment-idUSFWNOOL01D20140606.
[No Author Listed], "Medical Cannabis Community Wants To Remain Apart," Medical Marijuana News, Apr. 3, 2013, 3 pages; Kitsap Peninsula Business Journal, available at: https://www.420magazine.com/community/threads/medical-cannabis-community-wants-to-remain-apart.186955/.
[No Author Listed], "Medical Marijuana For N.J. Children? It's All In Gov. Christie's Hands," CBS News New York, Jun. 27, 2013, 3 pages; https://www.cbsnews.com/newyork/news/medical-marijuana-for-n-j-children-its-all-in-gov-christies-hands/.
Oguni, H. et al., "Severe myoclonic epilepsy in infants—a review based on the Tokyo women's Medical University series of 84 cases," Brain Dev., 23:736-748 (2010).
Panikasiwill, D. et al., "An endogenous cannabinoid (2-AG) is neuroprotective after brain injury," Nature 413:527-531 (2001).
Pellicia, et al.. International Association for Cannabis as Medicine, IACM 3rd Conference on Cannabinoids in Medicine, Sep. 9-10, 2005, 2005 Conference on Cannabinoids in Medicine, 72 pages.
Potter, C., "Cannabis Extract Brings Hope for Children with Epilepsy," Dec. 3, 2013, 3 pages.
Purcarin, G. & NG, Y-T., "Experience in the use of clobazam in the treatment of Lennox-Gastaut syndrome," Ther Adv Neurol Disord 2014, vol. 7(3):169-176.
Ragona, F. et al., "Dravet syndrome: early clinical manifestations and cognitive outcome in 37 Italian patients," Brain Dev., 32:71-77 (2010).
Rowe, R. C. et al., "Handbook of Pharmaceutical Excipients," Pharmaceutical Press and American Pharmacists Association 2009, pp. 17-19; https://www.academia.edu/16731682/Handbook_of_Pharmaceutical_Excipients_6th_Edition.
Russo et al., "Upholding WAG/Rij Rats as a Model of Absence Epileptogenesis: Hidden Mechanisms and a New Theory on Seizure Development," Neuroscience and Biobehavioral Reviews, 71:388-408 (2016).
Specchio, L. M. & Beghi, E., "Should Antiepileptic Drugs Be Withdrawn in Seizure-Free Patients?" CNS Drugs, 18(4):201-212 (2004).
Stewart, K., "Families migrating to Colorado for a medical marijuana miracle," Nov. 11, 2013, 8 pages; https://archive.sltrib.com/article.php?id=57052556&itype=CMSID.
Stinchcomb, A. L. et al., "Human skin permeation of $\Delta 8$-tetrahydrocannabinol, cannabidiol and cannabinol," JPP 2004, 56: 291-297.
Thiel, E. A., "Managing Epilepsy in Tuberous Sclerosis Complex," J Child Neurol 2004;19:680-686.
Tose, L. V. et al., "Isomeric separation of cannabinoids by UPLC combined with ionic mobility mass spectrometry (TWIM-MS)—Part I," International Journal of Spectrometry, 418:112-121 (2017).
Trost, B. M. & Dogra, K., "Synthesis of (-)-$\Delta 9$-trans-Tetrahydrocannabinol: Stereocontrol via Mo-Catalyzed Asymmetric Allylic Alkylation Reaction," Organic Letters, 9(5):861-863 (2007).
Van Bakel et al., "The draft genome and transcriptome of *Cannabis sativa*," Genome Biology 2011, 12:R102, 18 pages; http://genomebiology.com/2011/12/10/R102 (Oct. 24, 2011).
Whittle et al., (2001). Prospects for New Cannabis-Based Prescription Medicines. Journal of Cannabis Therapeutics. 1(3-4); doi:10.1300/J175v01, 1(3-4), 23 pages.
Wilkey, R., "'Weed Wars': Five-Year-Old Takes Medical Marijuana On Reality Show (Video)", Dec. 10, 2011, 7 pages; https://www.huffpost.com/entry/weed-wars-five-year-old-smokes-marijuana_n_1140351.
Young, S., "Marijuana stops child's severe seizures," CNN Health online, Aug. 7, 2013, 4 pages; https://www.cnn.com/2013/08/07/health/charlotte-child-medical-marijuana/index.html#:~:text=The%20first%20time%20Paige%20Figi,seizures%20stopped%20for%20seven%20days.&text=The%20marijuana%20strain%20Charlotte%20and,has%20been%20named%20after%20her.

* cited by examiner

USE OF CANNABINOIDS IN THE TREATMENT OF EPILEPSY

CROSS-REFERENCE TO RELATED APPLICATIONS

This application is a Continuation of U.S. patent application Ser. No. 17/119,873, filed Dec. 11, 2020; which is a Continuation of U.S. patent application Ser. No. 16/791,940, filed Feb. 14, 2020; which is a Continuation of U.S. patent application Ser. No. 15/948,412, filed Apr. 9, 2018, now U.S. Pat. No. 10,603,288, issued Mar. 31, 2020; which is a Continuation of U.S. patent application Ser. No. 15/449,084, filed Mar. 3, 2017, now U.S. Pat. No. 9,956,183, issued May 1, 2018; which is a Continuation of U.S. patent application Ser. No. 15/284,766, filed Oct. 4, 2016, now U.S. Pat. No. 9,949,936 issued Apr. 24, 2018; which is a Continuation of U.S. patent application Ser. No. 14/741,783, filed Jun. 17, 2015, now U.S. Pat. No. 9,474,726 issued Oct. 25, 2016; which claims the benefit of priority of GB 1506550.1, filed Apr. 17, 2015, and GB 1410771.8, filed Jun. 17, 2014, each of which incorporated herein by reference in their entireties.

FIELD OF THE INVENTION

The present invention relates to the use of cannabidiol (CBD) for the reduction of total convulsive seizure frequency in the treatment of "treatment-resistant epilepsy" (TRE). In one embodiment the patients suffering from TRE are children and young adults. CBD appears particularly effective when the TRE is Dravet syndrome; myoclonic absence seizures or febrile infection related epilepsy syndrome (FIRES). In these indications the reduction of total convulsive frequency has surprisingly been shown to be greater than 50%, through 70% to greater than 90% in a significant number of patients. Indeed a significant number of patients have been seizure free at the end of three months treatment.

Preferably the CBD used is in the form of a highly purified extract of *Cannabis* such that the CBD is present at greater than 98% of the total extract (w/w) and the other components of the extract are characterised. In particular tetrahydrocannabinol (THC) has been substantially removed to a level of not more than 0.15% (w/w). Alternatively, it is a synthetically produced CBD.

In use the CBD is used concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from "treatment-resistant epilepsy" (TRE).

Treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

One such childhood epilepsy is Dravet syndrome. Onset of Dravet syndrome almost always occurs during the first year of life with clonic and tonic-clonic seizures in previously healthy and developmentally normal infants (Dravet, 2011). Symptoms peak at about five months of age. Other seizures develop between one and four years of age such as prolonged focal dyscognitive seizures and brief absence seizures.

Seizures progress to be frequent and treatment-resistant, meaning that the seizures do not respond well to treatment. They also tend to be prolonged, lasting more than 5 minutes. Prolonged seizures may lead to status epilepticus, which is a seizure that lasts more than 30 minutes, or seizures that occur in clusters, one after another.

Prognosis is poor and approximately 14% of children die during a seizure, because of infection, or suddenly due to uncertain causes, often because of the relentless neurological decline. Patients develop intellectual disability and life-long ongoing seizures. Intellectual impairment varies from severe in 50% patients, to moderate and mild intellectual disability each accounting for 25°/s of cases.

There are currently no FDA approved treatments specifically indicated for Dravet syndrome. The standard of care usually involves a combination of the following anticonvulsants: clobazam, clonazepam, levetiracetam, topiramate and valproic acid.

Stiripentol is approved in Europe for the treatment of Dravet syndrome in conjunction with clobazam and valproic acid. In the US, stiripentol was granted an Orphan Designation for the treatment of Dravet syndrome in 2008; however, the drug is not FDA approved.

Potent sodium channel blockers used to treat epilepsy actually increase seizure frequency in patients with Dravet Syndrome. The most common are phenytoin, carbamazepine, lamotrigine and rufinamide.

Management may also include a ketogenic diet, and physical and vagus nerve stimulation. In addition to anti-convulsive drugs, many patients with Dravet syndrome are treated with anti-psychotic drugs, stimulants, and drugs to treat insomnia.

Common AED defined by their mechanisms of action are described in the following tables:

Examples of Narrow Spectrum AED

| Narrow-spectrum AED | Mechanism |
| --- | --- |
| Phenytoin | Sodium channel |
| Phenobarbital | GABA/Calcium channel |
| Carbamazepine | Sodium channel |
| Oxcarbazepine | Sodium channel |
| Gabapentin | Calcium channel |
| Pregabalin | Calcium channel |
| Lacosamide | Sodium channel |
| Vigabatrin | GABA |

Examples of Broad Spectrum AED

| Broad-spectrum AED | Mechanism |
| --- | --- |
| Valproic acid | GABA/Sodium channel |
| Lamotrigine | Sodium channel |
| Topiramate | GABA/Sodium channel |
| Zonisamide | GABA/Calcium/Sodium channel |
| Levetiracetam | Calcium channel |
| Clonazepam | GABA |
| Rufinamide | Sodium channel |

Examples of AED Used Specifically in Childhood Epilepsy

| AED | Mechanism |
| --- | --- |
| Clobazam | GABA |
| Stiripentol | GABA |

Over the past forty years there have been a number of animal studies on the use of the non-psychoactive cannabinoid cannabidiol (CBD) to treat seizures. For example, Consroe et al., (1982) determined that CBD was able to prevent seizures in mice after administration of pro-convulsant drugs or an electric current.

Studies in epileptic adults have also occurred in the past forty years with CBD. Cunha et al, reported that administration of CBD to eight adult patients with generalized epilepsy resulted in a marked reduction of seizures in 4 of the patients (Cunha et al., 1980).

A study in 1978 provided 200 mg/day of pure CBD to four adult patients, two of the four patients became seizure free, whereas in the remainder seizure frequency was unchanged (Mechoulam and Carlini, 1978).

In contrast to the studies described above, an open label study reported that 200 mg/day of pure CBD was ineffective in controlling seizures in twelve institutionalized adult patients (Ames and Cridland, 1986).

Based on the fact that chronologically the last study to look at the effectiveness of CBD in patients with epilepsy proved that CBD was unable to control seizures, there would be no expectation that CBD might be useful as an anti-convulsant agent.

In the past forty years of research there have been over thirty drugs approved for the treatment of epilepsy none of which are cannabinoids. Indeed, there appears to have been a prejudice against cannabinoids, possible due to the scheduled nature of these compounds and/or the fact that THC, which is a known psychoactive, has been ascribed as a pro-convulsant (Consroe et al., 1977).

A paper published recently suggested that cannabidiol-enriched Cannabis may be efficacious in the treatment of epilepsy. Porter and Jacobson (2013) report on a parent survey conducted via a Facebook group which explored the use of Cannabis which was enriched with CBD in children with treatment-resistant epilepsy. It was found that sixteen of the 19 parents surveyed reported an improvement in their child's epilepsy. The children surveyed for this paper were all taking Cannabis that was purported to contain CBD in a high concentration although the amount of CBD present and the other constituents including THC were not known. Indeed, whilst CBD levels ranged from 0.5 to 28.6 mg/kg/day (in those extracts tested), THC levels as high as 0.8 mg/kg/day were reported.

Providing children with TRE with a Cannabis extract that comprises THC, which has been described as a pro-convulsant (Consroe et al., 1977), in even small amounts, let alone at a potentially psychoactive dose of 0.8 mg/kg/day, is extremely dangerous and as such there is a real need to determine whether CBD is in fact efficacious.

To date there have been no controlled trials of CBD in children and young adults with TRE.

BRIEF SUMMARY OF THE DISCLOSURE

In accordance with a first aspect of the present invention there is provided cannabidiol (CBD) for use in the treatment of treatment-resistant epilepsy (TRE), wherein the epilepsy is febrile infection related epilepsy syndrome (FIRES).

In accordance with a second aspect of the present invention there is provided cannabidiol (CBD) for use in the treatment of epilepsy, wherein the epilepsy is a treatment-resistant epilepsy (TRE), and wherein the CBD is present in an amount that reduces total convulsive seizure frequency by greater than 50% with respect to the seizure frequency achieved on concomitant anti-epileptic drugs (AED).

Preferably the CBD is used in combination with two or more concomitant anti-epileptic drugs (AED). The CBD may be formulated for administration separately, sequentially or simultaneously with one or more AED or the combination may be provided in a single dosage form.

Preferably the seizure type to be treated is a complex partial seizure (focal seizure with impairment).

Preferably the CBD is present in an amount that reduces total convulsive seizure frequency by greater than 70% with respect to the seizure frequency achieved on concomitant anti-epileptic drugs (AED). More preferably the CBD is present in an amount that reduces total convulsive seizure frequency by greater than 90% with respect to the seizure frequency achieved on concomitant anti-epileptic drugs (AED). More preferably still the CBD is present in an amount that reduces total convulsive seizure frequency by 100% with respect to the seizure frequency achieved on concomitant anti-epileptic drugs (AED).

In one embodiment the CBD is present as a highly purified extract of Cannabis which comprises at least 98% (w/w) CBD.

The one or more AED is preferably selected from the group consisting of: clobazam; levetiracetam; topiramate; stiripentol; phenobarbital; lacsamide; valproic acid; zonisamide; perampanel; and fosphenytoin.

Preferably the CBD is used in combination with clobazam.

Preferably the number of different anti-epileptic drugs or the dose of AED that are used in combination with the CBD is reduced. More preferably the dose of AED which is reduced is of clobazam.

Preferably the dose of CBD is greater than 5 mg/kg/day. Thus for a 15 kg patient a dose of greater than 75 mg of CBD per day would be provided. Doses greater than 5 mg/kg/day such as greater than 10/mg/kg/day, greater than 15 mg/kg/day, greater than 20 mg/kg/day and greater than 25 mg/kg/day are also envisaged to be effective.

In accordance with a third aspect of the present invention there is provided a method of treating treatment-resistant epilepsy comprising administering cannabidiol (CBD) to a subject, wherein the epilepsy is febrile infection related epilepsy syndrome (ARES).

In accordance with a fourth aspect of the present invention there is provided a method of treating treatment-resistant epilepsy comprising administering cannabidiol (CBD) to a subject in an amount sufficient to reduce total convulsive seizure frequency by greater than 50% with respect to the seizure frequency achieved on one or more concomitant anti-epileptic drugs (AED).

Definitions

Definitions of some of the terms used to describe the invention are detailed below:

The cannabinoids described in the present application are listed below along with their standard abbreviations.

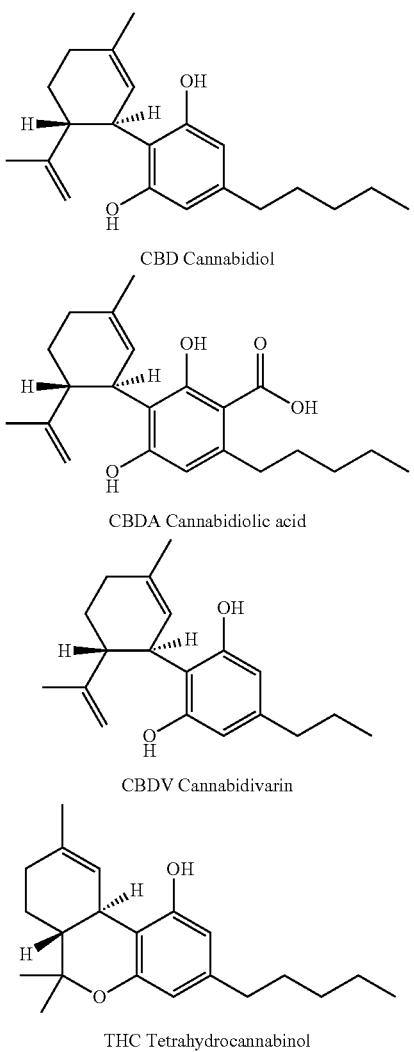

CBD Cannabidiol

CBDA Cannabidiolic acid

CBDV Cannabidivarin

THC Tetrahydrocannabinol

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *Cannabis* plant. The phytocannabinoids can be isolated from plants to produce a highly purified extract or can be reproduced synthetically.

"Highly purified cannabinoids" are defined as cannabinoids that have been extracted from the *Cannabis* plant and purified to the extent that other cannabinoids and non-cannabinoid components that are co-extracted with the cannabinoids have been removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (TRE) is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

DETAILED DESCRIPTION

Preparation of Highly Purified CBD Extract

The following describes the production of the highly-purified (>98% w/w) cannabidiol extract which has a known and constant composition which was used for the expanded access trials described in Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 98% CBD.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 1 below.

TABLE 1

CBD Specification

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| Impurities (Other Cannabinoids): | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT—Not more than

The purity of the CBD drug substance achieved is greater than 98%. The possible impurities are related cannabinoids: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally, furthermore during purification the stereochemistry of CBD is not affected.

Production of the Intermediate

An overview of the steps to produce a botanical extract, the intermediate, are as follows:
1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS) which was used for crystallisation to produce the test material.

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS.

Production of the Drug Substance

The manufacturing steps to produce the drug substance from the intermediate botanical extract are as follows:
1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis.

The dried product was stored in a freezer at minus 20° C. in a pharmaceutical grade stainless steel container, with FDA food grade approved silicone seal and clamps.

Examples 1 to 3 below describe the use of a highly purified *Cannabis* extract comprising cannabidiol (CBD). Cannabidiol is the most abundant non-psychoactive cannabinoid in the *Cannabis* plant. Previous studies in animals have demonstrated that CBD has anticonvulsant efficacy in multiple species and models.

Example 1 describes data produced in an expanded access treatment program in children with TRE.

Examples 2 to 4 demonstrates the efficacy of CBD in children with Dravet syndrome, myoclonic absence seizures and FIRES respectively.

Example 1: Efficacy of Cannabidiol in Children and Young Adults with Treatment-Resistant Epilepsy Materials and Methods Twenty-seven children and young adults with severe, childhood onset treatment-resistant epilepsy (TRE) were tested with a highly purified extract of cannabidiol (CBD) obtained from a *Cannabis* plant. The participants in the study were part of an expanded access compassionate use program for CBD.

All patients entered a baseline period of 4 weeks when parents/caregivers kept prospective seizure diaries, noting all countable motor seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after 4, 8 and 12 weeks of CBD therapy.

Results

There were 27 children and young adult patients who received at least 3 months of treatment all of whom suffered from treatment-resistant epilepsy.

All patients were taking at least two concomitant anti-epileptic drugs. These included clobazam; levetiracetam; topiramate; stiripentol; phenobarbital; lacsamide; valproic acid; zonisamide. The average number of concomitant anti-epileptic drugs being taken was 2.7. The majority took either clobazam and/or valproic acid.

Co-treatment of CBD with clobazam was a significant predictor of a positive treatment response of greater than 50% responder rate. There was an odds ratio (OR) of 3.3 for total seizure reduction and of 1.9 for convulsive seizures. The OR evaluates whether the odds of a certain event or outcome is the same for two groups. Specifically, the OR measures the ratio of the odds that an event or result will occur to the odds of the event not happening. An OR greater than 1 signifies that patients treated with a combination of CBD with clobazam will have a better odds of having a positive reduction in seizures than if they were not taking this combination of medications.

The median number of seizures that these patients suffered from before starting treatment was 30 seizures per month, with a range of 4 to 2,800 seizures per month being recorded.

Efficacy results for the 27 patients are summarized in Table 2 below.

TABLE 2

Changes in Seizure Frequency with CBD Therapy

| All patients | Month 3 (n = 27) |
|---|---|
| Responder rate (>50% reduction) [%] | 13 [48%] |
| Responder rate (>70% reduction) [%] | 11 [41%] |
| Responder rate (>90% reduction) [%] | 6 [22%] |
| Seizure free [%] | 2 [7%] |

Table 2 shows that after 3 months of therapy, 48% of patients had an equal to or greater than >50% reduction in seizures.

Remarkably, two of the patients, equating to 7%, were entirely free from seizures at the three month stage.

None of the 27 subjects withdrew during the 3-month treatment period and adverse events were mild and well tolerated. Common adverse events included somnolence, fatigue, decreased appetite, increased appetite and diarrhoea.

In five subjects their dose of clobazam was reduced due to its sedative effect.

Conclusions

These preliminary results indicate that CBD significantly reduces the number of seizures in a high proportion of patients that do not respond well to existing AED. The cannabidiol was generally well-tolerated in doses up to 25 mg/kg/day.

It was surprising that in this group of patients which are treatment-resistant such a high number were able to gain an effect. The fact that nearly half of the patients (48%) benefitted from at least a fifty percent reduction in the number of seizures that they suffered from was remarkable.

Furthermore, nearly a quarter (22%) of patients whose seizures were not controlled with at least two anti-epileptic drugs, experienced a reduction of 90% of the number of seizures they were experiencing and 7% were completely seizure free at the end of the 3 month trial period.

Even more remarkable were the results for some defined sub-sets of this generic group and these are set out on Examples 2 to 4 below.

Example 2: Efficacy of Cannabidiol in Children and Young Adults with Treatment Resistant Dravet Syndrome Materials and Methods Nine children and young adults with treatment-resistant Dravet syndrome were part of an expanded access compassionate use program for highly purified CBD extract as described in Example 1.

Results

All nine patients with Dravet syndrome were taking at least two concomitant anti-epileptic drugs. These were largely AED operating via GABA and included clobazam; levetiracetam; topiramate; stiripentol; phenobarbital; lacsamide; valproic acid; and zonisamide. The average number of concomitant antiepileptic drugs being taken was 2.7.

The mean number of seizures that these patients suffered from before starting treatment was 35 seizures per month, with a range of 6 to 112 seizures per month recorded.

Efficacy results for the 9 patients are summarized in Table 3 below.

TABLE 3

Changes in Seizure Frequency with CBD Therapy in Dravet Syndrome patients

| | Dravet patients (n = 9) | All patients (n = 27) | All patients excluding Dravet patients (n = 18) |
|---|---|---|---|
| Responder rate (>50% reduction) [%] | 5 [56%] | 13 [48%] | 8 [44%] |
| Responder rate (>70% reduction) [%] | 4 [44%] | 11 [41%] | 7 [39%] |
| Responder rate (>90% reduction) [%] | 3 [33%] | 6 [22%] | 3 [17%] |
| Seizure free [%] | 2 [22%] | 2 [7%] | 0 |

Table 3 shows that after 3 months of therapy, 56% of patients had an equal to or greater than 50% reduction in seizures, a third had a 90% reduction and remarkably 22%, were entirely free from seizures at the three month stage.

None of the 9 subjects withdrew during the 3-month treatment period and adverse events were mild and well tolerated. Common adverse events included somnolence, fatigue, decreased appetite, increased appetite and diarrhoea.

Conclusions

These data demonstrate that in this sub-group of patients with treatment-resistant Dravet syndrome a surprisingly high number were able to gain a dramatic reduction in the number of seizures.

Nearly a quarter (22%) of patients were entirely seizure free at the end of the 3 month trial period. This would not be expected in this group of patients who were taking a large number of different anti-epileptic medications and yet were still suffering from a large number of seizures per day.

Example 3: Efficacy of Cannabidiol in Children and Young Adults with Treatment Resistant Myoclonic Absence Seizures Materials and Methods Four children and young adults with treatment-resistant myoclonic absence seizures were part of an expanded access compassionate use program for highly purified CBD extract as described in Example 1.

Results

All four patients with myoclonic absence seizures were taking at least two concomitant anti-epileptic drugs. These were largely AED operating via GABA and included clobazam; levetiracetam; topiramate; stiripentol; phenobarbital; lacsamide; valproic acid; and zonisamide. The average number of concomitant antiepileptic drugs being taken was 27.

Efficacy results for the four patients are summarized in Table 4 below.

TABLE 4

Changes in Seizure Frequency with CBD Therapy in patients with myoclonic absence seizures (MAS)

| | MAS patients (n = 4) | All patients (n = 27) | All patients excluding MAS patients (n = 23) |
|---|---|---|---|
| Responder rate (>50% reduction) [%] | 2 [50%] | 13 [48%] | 11 [48%] |
| Responder rate (>70% reduction) [%] | 2 [50%] | 11 [41%] | 9 [39%] |
| Responder rate (>90% reduction) [%] | 1 [25%] | 6 [22%] | 5 [22%] |
| Seizure free [%] | 0 | 2 [7%] | 2 [9%] |

Table 4 shows that after 3 months of therapy, half of the patients had an equal to or greater than 50% reduction in seizures, one patient (25%) had a 90% reduction at the three month stage.

None of the 4 subjects withdrew during the 3-month treatment period and adverse events were mild and well tolerated. Common adverse events included somnolence, fatigue, decreased appetite, increased appetite and diarrhoea.

Conclusions

These data demonstrate that in this sub-group of patients with treatment-resistant MAS a surprisingly high number were able to gain a reduction in the number of seizures.

Example 4: Efficacy of Cannabidiol in Children with Treatment Resistant Febrile Infection Related Epilepy Syndrome (FIRES)

Febrile Infection Related Epilepsy Syndrome (FIRES) is a catastrophic epileptic encephalopathy with an unidentified aetiology that comprises a small minority of all patients with refractory status epilepticus.

This syndrome occurs in previously healthy children with 66-100% of survivors becoming developmentally disabled. The mortality rate is up to 30%. There is a critical need for new therapies to treat this condition.

Materials and Methods

Three patients with FIRES, with an age range of from 4 to 15 years, were treated with CBD under an expanded access program as described previously in Example 1.

Safety laboratory studies, physical/neurological exams, 24 hour video/EEG and seizure types and frequencies were assessed at baseline and one month after starting CBD.

A highly purified extract of CBD as an oral solution in sesame oil was used at a concentration of 25 mg/mL.

Treatment was initiated at a dose of 10 mg/kg/day given in two divided doses, increasing by 5 mg/kg/day every 3 days.

Following seizure improvement an average of 2 AEDs were weaned.

Results

Prior to initiation of treatment with highly purified CBD, the patients all suffered from refractory seizures or status epilepticus. These had been treated with anaesthetics including midazolam infusion, pentobarbital infusion, propofol infusion, and isofluorane infusion, additionally patients also were given steroids including lidocaine infusion, and methylprednisolone and other treatments including ketamine, fosphenytoin, thiamine, rituximab, cyclophosphamide, intravenous immunoglobulin, and a hypothermia protocol.

At the time of initiation of CBD, the patients were taking between three and five anti-epileptic drugs including: levetiracetam, clobazam, perampanel, phenobarbital, phenytoin, carbamezapine, felbamate, ketogenic diet, lamotrigine, valproic acid and vagus nerve stimulation therapy.

Baseline 24 hour EEG of seizures were recorded. The total seizures at baseline and during the treatment period are shown in Table 5. Patient 1 was shown to be seizure free after starting treatment for almost all of the treatment period, with the number of seizures being reduced from 7 to 0.3 over a 24 week period. Patient 2 had a 50% reduction in seizures after 4 weeks however the seizure frequency increased after a further 4 weeks then started to decrease again after 16 weeks of treatment. The most remarkable response was seen in Patient 3, who suffered from 5600 seizures at baseline. The number of seizures were dramatically reduced after 4 weeks and at week 24 this patient was still demonstrating a greater than 90% reduction in the number of seizures.

The type of seizures that occurred in the three FIRES patients were all complex partial seizures (focal seizures with impairment). None of the FIRES patients suffered from focal seizures with secondary generalisation or convulsive seizures.

TABLE 5

Total Seizure Data

| Visit | Frequency (per month) | Change from Baseline | % Change from Baseline | Responder (> = 50% Reduction) | Responder (> = 70% Reduction) | Responder (> = 90% Reduction) | Seizure Free |
|---|---|---|---|---|---|---|---|
| Patient 1 | | | | | | | |
| BL | 4.0 | n/a | n/a | n/a | n/a | n/a | n/a |
| Wk 4 | 0.0 | −4.0 | −100.0 | Yes | Yes | Yes | Yes |
| Wk 8 | 1.0 | −3.0 | −75.0 | Yes | Yes | No | No |

TABLE 5-continued

Total Seizure Data

| Visit | Frequency (per month) | Change from Baseline | % Change from Baseline | Responder (>= 50% Reduction) | Responder (>= 70% Reduction) | Responder (>= 90% Reduction) | Seizure Free |
|---|---|---|---|---|---|---|---|
| Wk 12 | 0.0 | −4.0 | −100.0 | Yes | Yes | Yes | Yes |
| Wk 16 | 0.0 | −4.0 | −100.0 | Yes | Yes | Yes | Yes |
| Wk 24 | 0.3 | −3.7 | −92.0 | Yes | Yes | Yes | No |
| Patient 2 | | | | | | | |
| BL | 7.0 | n/a | n/a | n/a | n/a | n/a | n/a |
| Wk 2 | 0.8 | −6.2 | −88.6 | Yes | Yes | No | No |
| Wk 4 | 3.0 | −4.0 | −57.1 | Yes | No | No | No |
| Wk 8 | 10.0 | 3.0 | 42.9 | No | No | No | No |
| Wk 12 | 8.0 | 1.0 | 14.3 | No | No | No | No |
| Wk 16 | 4.0 | −3.0 | −42.9 | No | No | No | No |
| Patient 3 | | | | | | | |
| BL | 5600.0 | n/a | n/a | n/a | n/a | n/a | n/a |
| Wk 4 | 47.2 | −5552.8 | −99.2 | Yes | Yes | Yes | No |
| Wk 8 | 9.2 | −5590.8 | −99.8 | Yes | Yes | Yes | No |
| Wk 12 | 141.6 | −5458.4 | −97.5 | Yes | Yes | Yes | No |
| Wk 24 | 542.0 | −5058.0 | −90.3 | Yes | Yes | Yes | No |

Follow up laboratory tests showed no changes in safety studies or concomitant AED levels. No treatment related adverse effects were observed.

Conclusions

CBD treatment was very well tolerated and associated with a dramatic and nearly immediate greater than 90% improvement in clinical and electrographic seizure burden in two of the three children with refractory seizures or status epilepticus due to FIRES.

After a reduction in seizures the patients were able to walk and verbalise once more.

Summary Table and Conclusions

Table 6 below summarises the data obtained in the three sub-sets: Dravet syndrome; myoclonic absence seizures (MAS) and febrile infection related epilepsy syndrome (FIRES) after 12 weeks of treatment which have been described in the Examples 2 to 4 above. In addition the data for the remainder of the patients with other epilepsy syndromes are detailed. These data which exclude the patients with Dravet, MAS and FIRES show a far lower responder rate than for the specified sub-sets of the above specified sub-sets of epilepsy.

In particular, the responder rate for patients obtaining a greater than 90% reduction in their seizures is reduced from 33% in Dravet patients to only 8% in the unspecified group. This suggests that patients suffering from a TRE of sub-type Dravet syndrome, myoclonic absence seizures or FIRES will respond better to treatment with highly purified CBD than patients with other epilepsy sub-types.

TABLE 6

Changes in Seizure Frequency with CBD Therapy in patients with sub-type TRE and all patients excluding the sub-types.

| | All patients (excluding Dravet, MAS and FIRES) (n = 13) | Dravet patients (n = 9) | MAS patients (n = 4) | FIRES patients (n = 3) |
|---|---|---|---|---|
| Responder rate (>50% reduction) [%] | 5 [38%] | 5 [56%] | 2 [50%] | 2 [67%] |
| Responder rate (>70% reduction) [%] | 4 [31%] | 4 [44%] | 2 [50%] | 2 [67%] |
| Responder rate (>90% reduction) [%] | 1 [8%] | 3 [33%] | 1 [25%] | 2 [67%] |
| Seizure free [%] | 0 | 2 [22%] | 0 | 1 [33%] |

REFERENCES

Ames F R and Cridland S (1986). "Anticonvulsant effects of cannabidiol." S Afr Med J 69:14.

Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8

Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85

Dravet C. The core Dravet syndrome phenotype. Epilepsia. 2011 April; 52 Suppl 2:3-9.

Eadie, M J (December 2012). "Shortcomings in the current treatment of epilepsy." Expert Review of Neurotherapeutics 12 (12): 1419-27.

Kwan P, Arzimanoglou A, Berg A T, Brodie M J, Hauser W A, Mathern G, Moshe S L, Perucca E, Wiebe S, French J. (2009) "Definition of drug resistant epilepsy: Consensus proposal by the ad hoc Task Force of the ILAE Commission on Therapeutic Strategies." Epilepsia.

Mechoulam R and Carlini E A (1978). "Toward drugs derived from *Cannabis*." Die naturwissenschaften 65:174-9.

Porter B E, Jacobson C (December 2013). "Report of a parent survey of cannabidiol-enriched *Cannabis* use in paediatric treatment resistant epilepsy" Epilepsy Behaviour. 29(3) 574-7

Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." Epilepsia. 52 Suppl 7: 2-26

The invention claimed is:

1. A method of treating seizures associated with a type of treatment-resistant epilepsy, which is Lennox-Gastaut syndrome or Dravet syndrome, in a patient in need thereof, comprising administering to the patient a pharmaceutical composition comprising a cannabidiol (CBD) drug substance and testing liver function,
   wherein the CBD drug substance comprises at least 98% w/w CBD, and
   wherein the CBD is administered at a starting dose of about 5 mg/kg/day, and then the dose is increased by increments of about 5 mg/kg.

2. The method of claim 1, wherein the dose of CBD is increased up to a maximum of about 25 mg/kg/day.

3. The method of claim 1, wherein the dose of CBD is increased to about 10 mg/kg/day.

4. The method of claim 1, wherein the dose of CBD is increased to about 20 mg/kg/day.

5. The method of claim 1, wherein the dose of CBD is increased to a dose ranging from about 10 mg/kg/day to about 20 mg/kg/day.

6. The method of claim 1, wherein the CBD is synthetic.

7. The method of claim 1, wherein the CBD drug substance comprises not more than 0.15% w/w Δ$^9$THC.

8. The method of claim 1, wherein the CBD drug substance comprises not more than 0.15% w/w CBDA, not more than 1.0% w/w CBDV, not more than 0.15% w/w Δ9THC, and not more than 0.5% w/w CBD-C4.

9. The method of claim 1, wherein the administering treats convulsive seizures.

10. The method of claim 1, wherein the administering reduces seizure frequency.

11. The method of claim 1, wherein the administering reduces total convulsive seizure frequency by at least 50% compared to the number of convulsive seizures experienced during a baseline period before CBD was administered.

12. The method of claim 3, wherein the administering treats convulsive seizures.

13. The method of claim 3, wherein the administering reduces seizure frequency.

14. The method of claim 3, wherein the administering reduces convulsive seizure frequency by at least 50% compared to the number of convulsive seizures experienced during a baseline period before CBD was administered.

15. The method of claim 4, wherein the administering treats convulsive seizures.

16. The method of claim 4, wherein the administering reduces seizure frequency.

17. The method of claim 4, wherein the administering reduces convulsive seizure frequency by at least 50% compared to the number of convulsive seizures experienced during a baseline period before CBD was administered.

18. The method of claim 1, wherein the type of treatment-resistant epilepsy is Lennox-Gastaut syndrome, and the dose of the CBD is increased to about 10 mg/kg/day or about 20 mg/kg/day.

19. The method of claim 18, wherein the patient's convulsive seizure frequency is reduced by at least 50% compared to the number of convulsive seizures experienced during a baseline period before CBD was administered.

20. The method of claim 18, wherein the dose of the CBD is increased to about 10 mg/kg/day.

21. The method of claim 18, wherein the dose of the CBD is increased to about 20 mg/kg/day.

22. The method of claim 1, wherein the type of treatment-resistant epilepsy is Dravet syndrome, and the dose of the CBD is increased to about 10 mg/kg/day or about 20 mg/kg/day.

23. The method of claim 22, wherein the patient's convulsive seizure frequency is reduced by at least 50% compared to the number of convulsive seizures experienced during a baseline period before CBD was administered.

24. The method of claim 22, wherein the dose of the CBD is increased to about 10 mg/kg/day.

25. The method of claim 22, wherein the dose of the CBD is increased to about 20 mg/kg/day.

26. The method of claim 1, wherein the testing is performed at baseline.

27. The method of claim 1, wherein the testing is performed after administering the CBD drug substance.

28. The method of claim 27, wherein the testing is performed 4 weeks or 12 weeks after initiating treatment.

29. The method of claim 1, wherein the testing is performed at baseline and after administering the CBD drug substance.

30. The method of claim 29, wherein the testing is performed after 4 weeks or 12 weeks of treatment.

* * * * *